(12) United States Patent
Fukumoto et al.

(10) Patent No.: US 7,425,455 B2
(45) Date of Patent: Sep. 16, 2008

(54) BIOSENSOR, MAGNETIC MOLECULE MEASUREMENT DEVICE

(75) Inventors: Hirofumi Fukumoto, Fuji (JP); Masayuki Nomura, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/502,759

(22) PCT Filed: Jan. 29, 2003

(86) PCT No.: PCT/JP03/00847

§ 371 (c)(1),
(2), (4) Date: Jul. 28, 2004

(87) PCT Pub. No.: WO03/067258

PCT Pub. Date: Aug. 14, 2003

(65) Prior Publication Data

US 2005/0106758 A1       May 19, 2005

(30) Foreign Application Priority Data

Jan. 29, 2002   (JP)   ............... 2002-020095
Sep. 18, 2002   (JP)   ............... 2002-271410

(51) Int. Cl.
*G01N 33/536* (2006.01)

(52) U.S. Cl. ............... 436/526; 436/518; 436/524; 422/68.1; 422/73; 435/4; 435/7.1; 435/283.1; 435/287.2

(58) Field of Classification Search ............... 436/526, 436/518, 524, 73; 422/68.1, 50, 61, 73; 435/4, 435/7.1, 283.1, 287.2
See application file for complete search history.

(56) References Cited

U.S. PATENT DOCUMENTS 5,107,460 A * 4/1992 Matthews .............. 365/122

(Continued)

FOREIGN PATENT DOCUMENTS

JP   63-090765   4/1988

(Continued)

OTHER PUBLICATIONS

R.L. Edelstein et al., "The BARC biosensor applied to the detection of biological warfare agents," Biosensors & Bioelectronics, Elsevier Science Publishers, Barking, GB, vol. 14, No. 10/11, Jan. 2000, pp. 805-813—XP-001069427.

(Continued)

*Primary Examiner*—Bao-Thuy L. Nguyen
*Assistant Examiner*—Melanie J Yu
(74) *Attorney, Agent, or Firm*—Finnegan, Henderson, Farabow, Garrett & Dunner, L.L.P.

(57) ABSTRACT

A biosensor not requiring washing of an unbonded label molecular by analyzing an object to be measured such as an antigen, an antibody, a DNA, and an RNA through magnetic field sensing. The biosensor is small in size, low in price, and high in sensing accuracy. Semiconductor Hall devices are arrayed two-dimensionally on the bottoms of recesses in the surface of a sensor chip to which bonded is a magnetic molecule with which a magnetic particle is labeled so as to sense the magnetic field produced along the sensor surface of the sensor chip. The surface area of each semiconductor Hall device is less than the maximum cross section of the magnetic molecule, and the intervals of the arrayed semiconductor Hall devices are larger than the diameter of the magnetic Hall molecule. Thus, the analysis accuracy is enhanced. An interconnection is used commonly to the semiconductor Hall devices, thereby reducing the size of the sensor.

19 Claims, 15 Drawing Sheets

U.S. PATENT DOCUMENTS

| | | | |
|---|---|---|---|
| 5,242,828 A * | 9/1993 | Bergstrom et al. | 435/287.1 |
| 5,981,297 A | 11/1999 | Baselt | |
| 6,437,563 B1 | 8/2002 | Simmonds | |
| 6,743,639 B1 | 6/2004 | Tondra | |
| 6,768,301 B1 | 7/2004 | Hohe | |
| 2001/0041349 A1 * | 11/2001 | Patron et al. | 435/7.92 |
| 2001/0052769 A1 | 12/2001 | Simmonds | |
| 2001/0052770 A1 | 12/2001 | Simmonds | |
| 2002/0060565 A1 | 5/2002 | Tondra | |
| 2002/0086443 A1 * | 7/2002 | Bamdad | 436/526 |
| 2002/0119470 A1 | 8/2002 | Nerenberg | |
| 2003/0082587 A1 * | 5/2003 | Seul et al. | 435/6 |
| 2004/0033627 A1 * | 2/2004 | Aytur et al. | 436/526 |
| 2004/0150396 A1 | 8/2004 | Simmonds | |
| 2004/0219695 A1 * | 11/2004 | Fox | 436/526 |
| 2004/0259271 A1 | 12/2004 | Tondra | |
| 2005/0087000 A1 | 4/2005 | Tondra | |
| 2005/0127916 A1 | 6/2005 | Tondra | |

FOREIGN PATENT DOCUMENTS

| | | | |
|---|---|---|---|
| JP | 63-302367 | | 12/1988 |
| TW | 86104580 | | 4/1999 |
| WO | 97-45740 | | 12/1997 |
| WO | WO 01/18556 | * | 3/2001 |

OTHER PUBLICATIONS

J. Richardson et al., "The use of coated paramagnetic particles as a physical label in a magneto-immunoassay," Biosensors & Bioelectronics, Elsevier Science Publishers, Barking, GB, vol. 16, No. 9-12, Dec. 2001, pp. 989-993—XP-002334351.

Julie Richard et al., "A novel measuring system for the determination of paramagnetic particle labels for use in magneto-immunoassays," Biosensors & Bioelectronics, Elsevier Science Publishers, Barking, GB, vol. 16, No. 9-12, Dec. 2001, pp. 1127-1132—XP-002334352.

Keiji Enpuku, "Detection of Magnetic Nanoparticles wth SQUID and Application to Biological Immunoassays," The Society of Non-Traditional Technology: Forum of Superconductivity, Science and Technology News, No. 81, pp. 1-4, (Aug. 15, 2000).

* cited by examiner

| No. 1 | No. 2 | No. 3 | No. 4 | No. 5 |
|-------|-------|-------|-------|-------|
| 0.996 | 1.045 | 1.000 | 1.004 | 1.053 |

|  | No. 1 | No. 2 | No. 3 | No. 4 | No. 5 |
|---|---|---|---|---|---|
| Pre-binding (mV) | 882 | 886 | 885 | 887 | 886 |
| Post-binding (mV) | 882 | 887 | 885 | 892 | 887 |
| Difference (mV) | 0 | 1 | 0 | 5 | 1 |

BIOSENSOR, MAGNETIC MOLECULE MEASUREMENT DEVICE

CROSS-REFERENCE TO RELATED APPLICATIONS

This application is a National Stage application under 35 U.S.C. §371 and claims benefit under 35 U.S.C. §119(a) of International Application No. PCT/JP03/00847 having an International Filing Date of Jan. 29, 2003, which claims benefit of JP 2002-20095 filed on Jan. 29, 2002 and JP 2002-271410 filed on Sep. 18, 2002.

TECHNICAL FIELD

The present invention relates to a biosensor, a method for measuring magnetic molecules and a method for measuring objects to be measured, and more particularly to a biosensor, a method for measuring magnetic molecules and a method for measuring objects to be measured that are used for analyzing objects to be measured by measuring the amount of magnetic molecules.

BACKGROUND ART

In recent years clinical diagnosis and detection as well as genetic analysis is being carried out by immunological techniques or hybridization in which specific binding between specific pairs of molecules, such as binding of an antigen to its antibody, is utilized to detect antigens, antibodies, DNA (DeoxyribonucleicAcid) molecules, RNA (RibonucleicAcid) molecules and the like.

Particularly in solid phase binding assay, a method is used that utilizes magnetic particles for detection. A schematic diagram of the conventional solid phase assay using magnetic particles is shown in FIG. 17.

As shown in the figure, the assay is performed using a solid phase 91, molecular receptors 61 that capture an object to be measured 62, a magnetic particle 51, and molecular receptors 63 which detect the object to be measured 62, to thereby assay the object to be measured 62.

The solid phase 91 has a solid phase surface that contacts with a sample solution, and the molecular receptors 61 are immobilized on the solid phase surface. A polystyrene bead, a wall surface of a reaction vessel, a substrate surface or the like is used for the solid phase.

As the molecular receptors 61 and the molecular receptors 63, a molecule that binds specifically to the object to be measured 62 that is present in the sample solution is used. The object to be measured 62 may be an antigen, antibody, DNA molecule, RNA molecule or the like.

The magnetic particle 51 is a labeling material having magnetization. Detecting a magnetic field produced by the magnetization of the magnetic particle makes it possible to determine the amount of the magnetic particle 51 that is in a state to be described hereinafter, and thus the presence or concentration of an object to be measured in the sample solution can be identified. In addition to the magnetic particle 51, a substance that emits a detectable signal, such as a radioactive substance, fluorophore, chemiluminophore, enzyme or the like, may be used as a label. Examples of known assay methods using these labels include Enzyme Immunoassay (EIA) which utilizes the reaction between an antigen and its antibody, or Chemiluminescence (CL) methods such as a strict Chemiluminescence Immunoassay (CLIA) in which a chemiluminescent compound is used as a labeling compound for immunoassay, or Chemiluminescence Enzyme Immunoassay (CLEIA) in which enzyme activity is detected at high sensitivity using a chemiluminescent compound in the detection system.

The molecular receptors 63 that are previously bound to the magnetic particle 51 are antibodies that bind specifically to the object to be measured 62 that is previously bound to the magnetic particle 51.

In the assay illustrated in the figure, first, a sample solution containing the object to be measured 62 is introduced onto the solid phase 91 on which the molecular receptors 61 were immobilized beforehand, whereby the object to be measured 62 specifically binds to the molecular receptor 61. Other substances contained in the sample solution float in the sample solution without binding to the solid phase 91. Then, the magnetic particle 51 on which the molecular receptors 63 are immobilized is introduced into the sample solution. Alternatively, the magnetic particle 51 on which the molecular receptors 63 are immobilized may be introduced into the sample solution at the same time as the object to be measured 62. Thereby, the molecular receptor 63 binds specifically to the object to be measured 62 that is bound specifically to the molecular receptor 61 immobilized on the solid phase. The magnetic particle 51 having the molecular receptors 63 immobilized thereon is referred to as a "magnetic molecule". Then, a magnetic field produced by the magnetic particle is detected, whereby the amount of magnetic particles 51 bound to the surface of the solid phase 91 is determined. Thus, it is possible to determine the concentration or position of the object to be measured 62 bound to the surface of the solid phase 91. With respect to detection of the magnetic field, detection methods using magnetoresistive elements arranged in an array are disclosed in U.S. Pat. No. 5,981,297 and International Patent Publication WO 97/45740.

In addition to the sandwich assay method described above in which an object to be measured binds specifically to a molecular receptor and a different molecule label then binds specifically to the object to be measured, examples of other assay methods utilizing the above labels include a competitive assay in which an object to be measured and another molecule label competitively bind to a molecular receptor.

In the conventional methods, a signal such as fluorescence or the like from a label is detected by an apparatus, such as an optical detection apparatus, that is capable of detecting the signal. In these methods, it is necessary to capture only the signal from the label of a molecule that is specifically bound to a binding molecule immobilized on a solid phase surface. However, in the case of optical detection, if an unbound labeled molecule is present, the signal from this label may also be captured and thus an accurate assay cannot be conducted.

Accordingly, it is necessary to completely wash away unbound labeling molecules. Further, since it is necessary for an optical detection apparatus to detect a faint light signal, it is difficult to produce a miniturized or low cost detection apparatus.

In the method for detection by magnetoresistive elements using magnetic particles as labels as disclosed in the above U.S. Pat. No. 5,981,297, it is not necessary to wash away any unbound labeling molecules. However, a detection chip on which magnetoresistive elements are arranged in an array requires the switching circuits in order to independently extract the signal of individual elements. Electrical wiring is then required respectively from each of the elements in the array to the switching circuits. Consequently, one problem therewith is that as the number of elements increases the wiring becomes more complicated and the area occupied by the wiring also increases, and thus miniaturization is difficult.

In the aforementioned International Patent Publication WO 97/45740, a circuit for detection of magnetic particles comprises a bridge circuit composed of magnetoresistive elements and transistors functioning as switching elements. However, since magnetoresistive elements require magnetic material, after fabricating a part of the circuit containing transistors by a standard integrated circuit production process, it is then necessary to conduct processes for forming and processing a magnetic thin film.

It is an object of the present invention to provide a biosensor that eliminate the need of washing away of unbound labeling molecules by analyzing an object to be measured such as an antigen, antibody, DNA molecule or RNA molecule through detection of a magnetic field, in which the biosensor is small in size, low in price, and high in sensing accuracy, as well as a method for measuring a magnetic molecule and a method for measuring an object to be measured.

DISCLOSURE OF THE INVENTION

According to the present invention there is provided a biosensor which assays an object to be measured by means of a magnetic sensor composed of detector elements for detecting a magnetic field produced by bound magnetic molecules, the detector elements being arranged two-dimensionally in X rows and Y columns (X and Y are natural numbers, the same applies hereunder) and the assay of the object to be measured being conducted by measuring the amount of the above magnetic molecules, characterized in that the biosensor comprises a signal processing means which determines the amount of the bound magnetic molecules by comparing the intensities of magnetic fields of different regions along the sensor surface of the magnetic sensor, and assay of the object to be measured is conducted based on the determined amount of magnetic molecules.

The present invention further provides the above biosensor characterized in that the detector element comprises a semiconductor Hall device.

The present invention further provides the above biosensor characterized in that a reference region to which the above magnetic molecules are incapable of binding is provided on the sensor surface of the above magnetic sensor, and the above signal processing means conducts comparison using an intensity of a magnetic field of the reference region as a reference.

As used herein, the term "mutually different regions" refers to, for example, comparing the respective intensities of magnetic fields detected by adjacent Hall devices. Alternatively, a region is provided as a reference, and the intensity of a magnetic field detected in that region may be used as a reference for comparison with the intensity of a magnetic field detected in another arbitrary region.

The present invention further provides the above biosensor characterized in that surface treatment is performed for the above reference region such that molecular receptors that bind with the magnetic molecules are incapable of immobilizing thereto.

The present invention further provides the above biosensor characterized in that it further comprises a selection means for selecting individual detector elements arranged in the above X rows and Y columns and extracting an output thereof.

The present invention further provides the above biosensor characterized in that the above magnetic sensor, the above selection means and a signal amplification circuit that amplifies an output signal of the above detector element are formed on one chip.

The present invention further provides the above biosensor characterized in that the size of each detection space in which detection of a magnetic field by the above detector elements is possible is equal to the size of approximately one molecule of the magnetic molecules to be bound.

Thereby, the number of magnetic molecules detected by a detector element is limited to one, and thus variations in measurement values caused by detection of a plurality of magnetic molecules can be controlled. This enables enhancement of the analysis accuracy.

The present invention further provides the above biosensor characterized in that in the above magnetic sensor, the detector elements are arranged at intervals such that two detector elements next to each other detect mutually different magnetic molecules.

Thus, it is possible to inhibit interference such as detection of the same magnetic molecule by adjacent detector elements.

The present invention still further provides the above biosensor characterized in that the above adjacent detector elements are arranged adjacent to each other at an interval that is equal to or greater than the diameter of the above magnetic molecules.

Thus, it is possible to inhibit interference such as detection of the same magnetic molecule by adjacent semiconductor Hall devices.

The present invention also provides the above biosensor characterized in that the sensor surface of the above magnetic sensor is subject to surface treatment for selectively immobilizing in a specified region molecular receptors that bind to the above magnetic molecules.

The present invention further provides the above biosensor characterized in that recesses of a size corresponding to the size of the above magnetic molecules are provided on the sensor surface of the above magnetic sensor, and that molecular receptors that bind to the magnetic molecules are provided only in the recesses on the sensor surface.

The present invention still further provides the above biosensor characterized in that a gold thin film is formed in the specified region on the sensor surface of the magnetic sensor, and the above molecular receptors that have an end modified by a thiol group are selectively immobilized thereon.

The present invention also provides the above biosensor characterized in that the biosensor comprises a first magnetic field generation means arranged in a position facing the sensor surface of the above magnetic sensor that generates a magnetic field that is applied to the sensor surface of the above magnetic sensor.

The present invention further provides the above biosensor characterized in that it comprises means whereby the above first magnetic field generation means intermittently generates a magnetic field.

The present invention still further provides the above biosensor characterized in that it comprises a detector circuit which, when the above first magnetic field generation means generates a magnetic field at a constant frequency, extracts only a frequency component corresponding to the magnetic field from an output signal of the above detector element.

The present invention further provides the above biosensor characterized in that the biosensor comprises a second magnetic field generation means arranged on the backside of a sensor surface of the above magnetic sensor for generating a magnetic field that is applied to the sensor surface of the above magnetic sensor.

The present invention further provides the above biosensor characterized in that the above second magnetic field generation means comprises means for intermittently generating a magnetic field.

The present invention further provides the above biosensor characterized in that the when the above second magnetic field generation means comprises a detector circuit for generating a magnetic field at a constant frequency, extracting only a frequency component corresponding to the magnetic field from an output signal of the above detector element.

The present invention further provides the above biosensor characterized in that the above magnetic sensor is arranged such that the sensor surface of the magnetic sensor faces in a direction in which gravitational force acts.

The present invention still further provides the above biosensor characterized in that the above semiconductor Hall device has a pair of current terminals, a gate electrode controlling current flowing between the current terminals, and a pair of output terminals arranged such that current flows roughly perpendicular to current flowing between the current terminals.

The present invention further provides the above biosensor characterized in that, in the above case, the above gate electrode is connected to a gate electrode wire that is common to the semiconductor Hall devices arranged in the same column, the above pair of current terminals are connected to a pair of current terminal wires that are common to the semiconductor Hall devices arranged in the same row, the above pair of output terminals are connected to a pair of output terminal wires that are common to the semiconductor Hall devices arranged in the same row, and the above selection means extracts an output signal of the semiconductor Hall device arranged in an arbitrary position by selecting the gate electrode wire, pair of current terminal wires, and pair of output terminal wires.

By providing interconnections that are common for each column and each row, respectively, selection of a semiconductor Hall device in an arbitrary position can be simply performed and, moreover, the number of interconnections can be reduced. Thus, production of a magnetic sensor according to an object to be measured sample is simplified, and miniaturization of a magnetic sensor is enabled.

According to a further aspect of the present invention there is provided a method for measuring magnetic molecules in which a magnetic sensor composed of detector elements for detecting a magnetic field produced by bound magnetic molecules, in which the detector elements are arranged two-dimensionally in X rows and Y columns (X and Y are natural numbers, the same applies hereunder), is used to determine an amount of the magnetic molecules, characterized in that the method comprises:

a measurement step for acquiring intensities of magnetic fields of mutually different regions of a sensor surface of the magnetic sensor; and a determination step for determining the amount of the bound magnetic molecules by comparing the intensities of the magnetic fields of the mutually different regions obtained in the measurement step.

The present invention further provides the above method for measuring magnetic molecules characterized in that in the above determination step, comparison is carried out taking as a reference the intensity of a magnetic field of a reference region to which magnetic molecules are incapable of binding that was obtained in the above measurement step.

According to another aspect of the present invention there is provided a method for measuring magnetic molecules in which a magnetic sensor composed of detector elements for detecting a magnetic field produced by bound magnetic molecules, in which the detector elements are arranged two-dimensionally in X rows and Y columns (X and Y are natural numbers, the same applies hereunder), is used to determine the amount of the magnetic molecules, characterized in that the method comprises:

a pre-binding measurement step for acquiring intensities of magnetic fields prior to binding of the magnetic molecules;

a post-binding measurement step for acquiring intensities of magnetic fields after binding of the magnetic molecules; and a determination step for determining the amount of the bound magnetic molecules by comparing the intensities of the magnetic fields prior to binding with the intensities of the magnetic fields after binding.

The present invention further provides the above method for measuring magnetic molecules characterized in that it further comprises an offset value acquisition step for acquiring an offset value that is output from the detector element.

The present invention still further provides the above method for measuring magnetic molecules characterized in that in the above measurement step, by means of a magnetic field applied at a constant frequency to the sensor surface, an output signal of a detector element is obtained that includes a signal output at a frequency corresponding to the magnetic field; and in the above determination step, comparison is conducted using a value obtained after removing an offset value included as a direct current component by extracting only a frequency component corresponding to the magnetic field from the output signal of a detector element obtained in the above measurement step.

The present invention also provides the above method for measuring magnetic molecules characterized in that it further comprises a binding acceleration step for generating a magnetic field for bringing the above magnetic molecules close to the sensor surface by a magnetic field generation means at the time of introducing the magnetic molecules to the sensor surface.

The present invention further provides the above method for measuring magnetic molecules characterized in that in the above binding acceleration step a magnetic field is applied of an intensity such that the magnetization of the above magnetic molecules becomes saturated, and in the above step of acquiring the intensity of a magnetic field, the magnetic field is applied of an intensity such that the magnetization of the magnetic molecules does not become saturated.

Here, a step for acquiring the intensity of a magnetic field is the above measurement step, the above post-binding measurement step or the above pre-binding measurement step or the like.

The present invention further provides the above method for measuring magnetic molecules, characterized in that the method further comprises a stirring step for stirring magnetic molecules, after introducing the above magnetic molecules to the sensor surface, by alternately producing magnetic fields by means of a first magnetic field generation means arranged in a position facing the sensor surface and a second magnetic field generation means arranged on the backside of the sensor surface.

The present invention also provides the above method for measuring magnetic molecules, characterized in that in the above stirring step a magnetic field is applied of an intensity such that magnetization of the magnetic molecules becomes saturated, and in a step for acquiring the intensity of a magnetic field a magnetic field is applied of an intensity such that magnetization of the magnetic molecules does not become saturated.

Here, a step for acquiring the intensity of a magnetic field is the above measurement step, the above post-binding measurement step or the above pre-binding measurement step or the like.

According to a further aspect of the present invention there is provided a method for measuring objects to be measured using a biosensor according to any of claims 1 to 20, characterized in that molecules that bind specifically to the objects to be measured for binding are used as the above magnetic molecules, the method comprising the steps of:

determining the amount of the magnetic molecules bound specifically to objects to be measured using a biosensor; and determining the amount of objects to be measured based on the amount of the magnetic molecules.

According to a still further aspect of the present invention there is provided a method for measuring objects to be measured using a biosensor according to any of claims 1 to 20, characterized in that molecules that are reversibly exchangeable for the objects to be measured for binding are used as the magnetic molecules, the method comprising the steps of:

determining an amount of the magnetic molecules bound in place of the objects to be measured using a biosensor; and determining the amount of the objects to be measured based on the amount of the magnetic molecules.

BEST MODE FOR CARRYING OUT THE INVENTION

Figure 1:
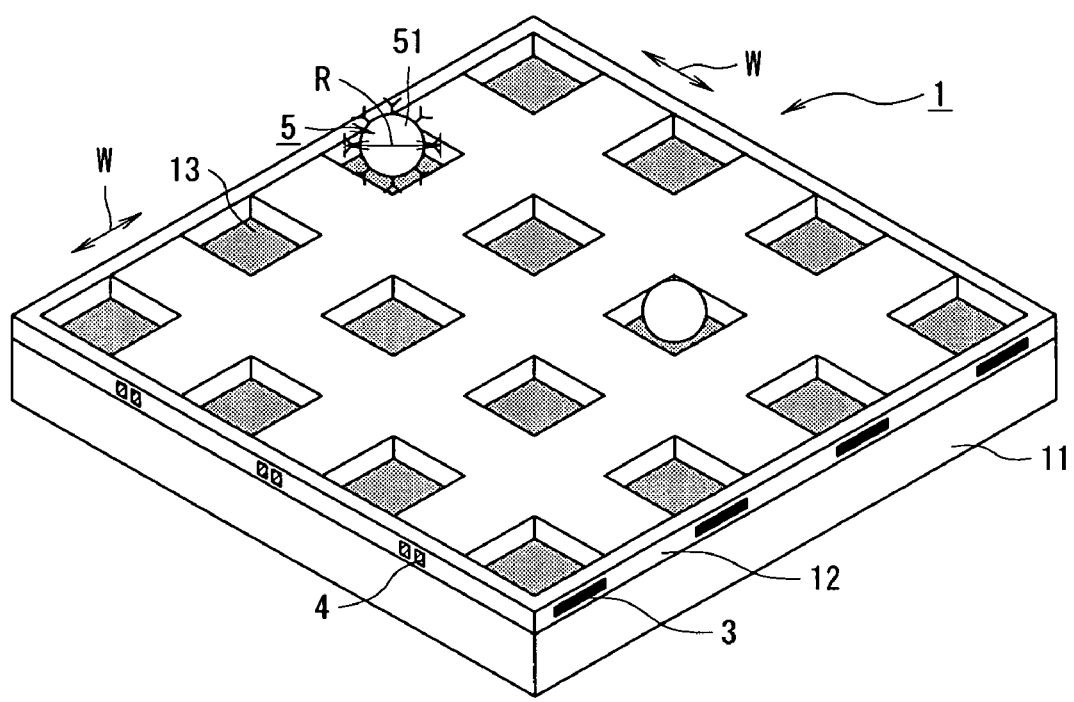
FIG. 1 is a view schematically showing a part of the biosensor of the present invention.

Now, embodiments of the present invention will be described referring to the drawings. In each of the drawings referred to in the following description, parts that are the same in other drawings are denoted using the same symbol.

Embodiment 1

FIG. 1 is a schematic diagram showing a part of a sensor chip comprising the biosensor of the present invention. The composition of a sensor chip 1 includes semiconductor Hall devices as detector elements and a signal processing circuit of the semiconductor Hall devices. The sensor chip 1 is produced as described hereunder.

The sensor chip 1 is formed on a silicon substrate 11 by well-known CMOS (complementary metal oxide semiconductor) processes. Semiconductor Hall devices are formed at the bottom of recesses 13 in the surface of the sensor chip 1. Input and output of each of the semiconductor Hall devices is conducted through a gate electrode 30 and a metal wire 4.

After forming semiconductor Hall devices and a signal processing circuit on the silicon substrate 11 by CMOS processes, molecular receptors such as antigens, antibodies, DNA molecules or RNA molecules are immobilized on the surface of the sensor chip 1 treated by a silane coupling agent or the like.

Then, a sample solution is dropped onto the surface of the sensor chip 1, and objects to be measured such as antigens, antibodies, DNA molecules or RNA molecules are bound to the molecular receptors on the surface of the sensor chip 1. Thereafter, magnetic particles on which antigens, antibodies, DNA molecules or RNA molecules or the like are bound are introduced onto the surface of the sensor chip 1, and are specifically bound on semiconductor Hall devices to which objects to be measured are specifically binding.

The semiconductor Hall device preferably has a detection space of a size that can accommodate one of the specifically binding magnetic molecules. More specifically, in this embodiment, a semiconductor Hall device preferably has a space capable of detecting a magnetic field produced by a magnetic molecule binding to a molecular receptor immobilized on the surface of the sensor chip 1. As used herein, the term "magneticmolecule" refers to a molecule that has magnetization. In this embodiment, a magnetic molecule is a molecule labeled with a magnetic particle having a molecular receptor attached thereto. Alternatively, the molecule itself has magnetization and can be detected by a semiconductor Hall device. In this embodiment, the surface area of a semiconductor Hall device 2 is of a size equal to that of the maximum cross-section area of a magnetic molecule.

Thus, it is possible to limit the number of magnetic molecules 5 that are present in a detection space to one. Therefore, when conducting measurement by detecting the presence or absence of one of the magnetic molecules 5 using one of the semiconductor Hall devices 2, it is possible to prevent detection of two or more of the magnetic molecules 5 by one semiconductor Hall device, thereby enabling accurate measurement. The present invention is not limited to a measurement method that is carried out by one semiconductor Hall device detecting the presence or absence of one magnetic molecule. More specifically, by making the size of the surface area of the semiconductor Hall device 2 equivalent to the maximum cross-section area of a plurality of magnetic molecules, one semiconductor Hall device may detect the presence of a plurality of magnetic molecules.

Further, as shown in FIG. 1, a similar effect can be obtained by providing recesses 13 in the detection spaces on the surface of the sensor chip 1, and making the area of the recesses 13 in correspondence to the size of the magnetic molecules 5 used in each measurement. For example, the recesses 13 may be provided at a size that is smaller than the maximum cross-section area of the magnetic molecules 5 described above. Molecular receptors are then provided only in the recesses 13. Thus, the quantity of the magnetic molecules 5 that are capable of binding to molecular receptors can be controlled by limiting the number of molecular receptors in the detection space regardless of the size of the semiconductor Hall devices. This configuration can be used when the magnetic molecules 5 are extremely minute in comparison to the size of the semiconductor Hall devices and it is not possible to reduce the size of the detection spaces. In this embodiment, the recesses 13 are constructed by providing the metal wire 4 on the surface where the semiconductor Hall devices are provided, however, for example, the recesses 13 may also be formed by etching after flattening the surface of the sensor chip 1. Molecular receptors can be immobilized only in the recesses 13 by first immobilizing molecular receptors to the sensor chip 1 and then wiping the surface of the sensor chip 1.

The present invention is not limited to a case of providing semiconductor Hall devices on the bottom of recesses as shown in FIG. 1, and semiconductor Hall devices may be provided such that the sensor chip surface is flat. However, by forming semiconductor Hall devices on the bottom of the recesses 13 in the sensor chip surface, in addition to the aforementioned effects, the following effects can also be obtained. That is, interference caused by magnetic molecules present at the boundary of a detection space of a semiconductor Hall device can be prevented by adjusting the binding conditions for magnetic molecules in regions detected by semiconductor Hall devices, or alternatively, the conditions for reaction between molecular receptors and magnetic molecules can be made uniform by immobilizing molecular receptors only in regions which are under the same conditions.

In this embodiment, semiconductor Hall devices are provided in the form of a two-dimensional array. In the sensor chip in this case, semiconductor Hall devices are arranged at intervals that are provided such that two adjacent semiconductor Hall devices detect mutually different magnetic molecules. Thus, it is possible to prevent interference among the individual semiconductor Hall devices. A similar effect can also be obtained by providing recesses corresponding to mutually different semiconductor Hall devices at the aforementioned intervals as explained above. As shown in FIG. 1, in this embodiment the recesses 13 corresponding to the respective semiconductor Hall devices are provided at an interval W that is larger than a diameter R of the magnetic molecule 5.

The following method may be used as a method for immobilizing molecular receptors such as antigens, antibodies, DNA molecules or RNA molecules on the surface of the sensor chip 1. Semiconductor Hall devices and a signal processing circuit are formed on the silicon substrate 11 by CMOS processes, and then a gold thin film is formed on the sensor chip surface. In order to improve adherence between the gold thin film and the sensor chip surface, a thin film of Cr, Ni, or Ti is preferably formed between the gold thin film and the surface of the sensor chip 1 as an adhesion layer.

After formation of the gold thin film, molecular receptors having ends modified with a thiol group are immobilized on the surface of the gold thin film. In this case, after formation of the gold thin film, it is also possible to immobilize thiol compounds on the surface of the gold thin film and then immobilize the molecular receptors thereon.

Further, a gold thin film may be formed only at positions corresponding to the locations of the semiconductor Hall devices shown by the recesses 13 in FIG. 1. Since thiol groups selectively bind with the gold thin film, it is possible to immobilize molecular receptors on only specific regions on the surface of the sensor chip 1.

A pattern of a gold thin film to be formed at specific positions can be formed by a so-called "lift-off method" in which a pattern is first formed by a photoresist, and subsequently a Ti thin film as an adhesion layer and a gold thin film are formed by sputtering, and the photoresist is then removed.

Figure 2:
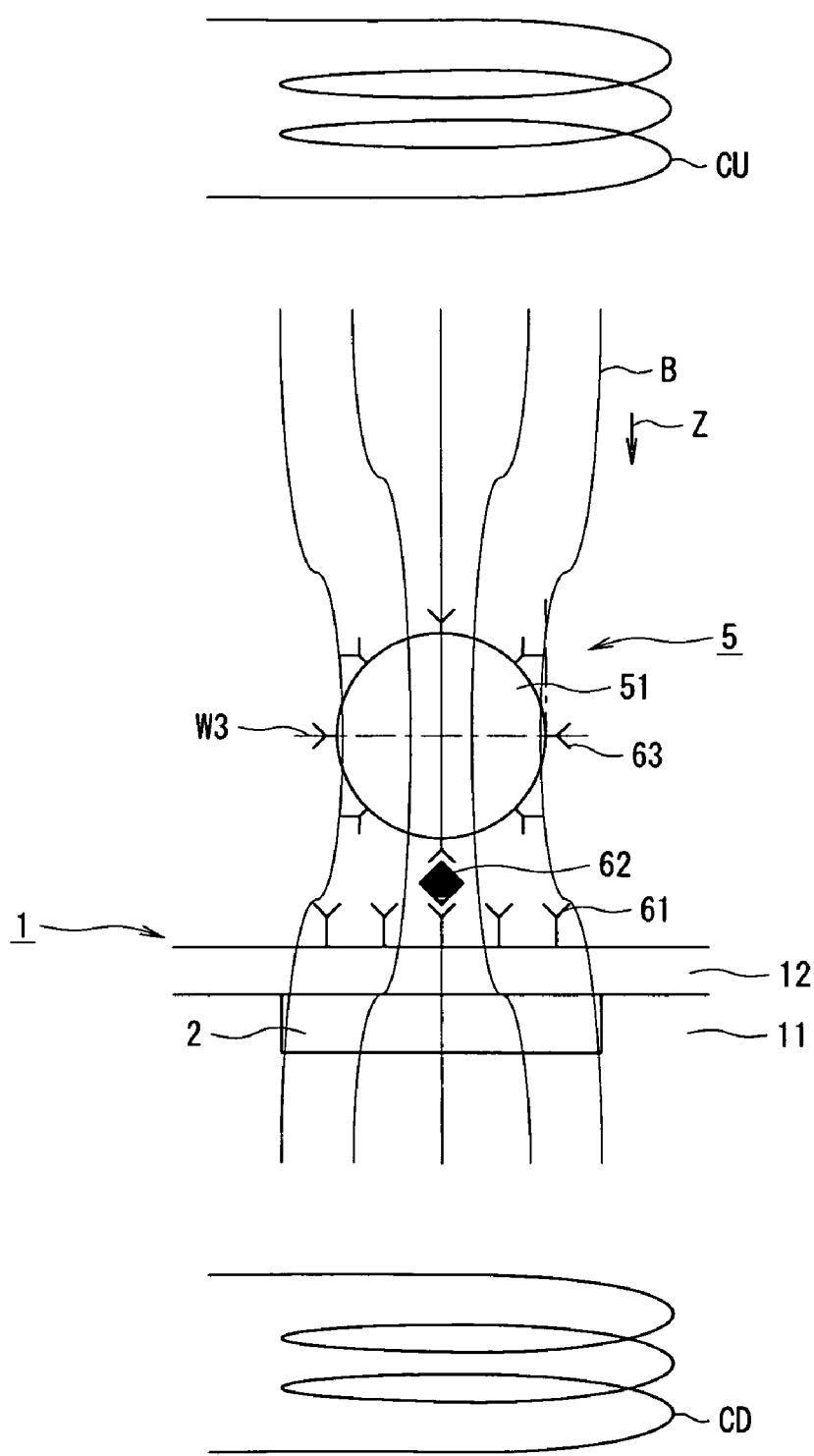
FIG. 2 is a view illustrating the detection principles of a biosensor according to a first and second embodiment herein.

Next, the detection principles of a biosensor according to the present invention will be explained using FIG. 2. FIG. 2 is a view that schematically shows a cross section of the vicinity of the semiconductor Hall device 2 on the sensor chip 1. Molecular receptors 61 composed of antibodies are immobilized on the surface of the semiconductor Hall device 2. An object to be measured 62 binds specifically to the molecular receptor 61, and a magnetic particle 51 further binds to the object to be measured 62 through specific binding between the object to be measured 62 and a molecular receptor 63 composed of an antibody. The magnetic particle 51 and the molecular receptors 63 bind to each other to form the magnetic molecule 5.

An upper coil CU (first magnetic field generation means) is arranged in a position facing the surface of the sensor chip 1. In a state where a magnetic molecule is bound to the surface of the sensor chip 1 as described above, a current is passed through the upper coil CU to generate a magnetic field. In place of a coil, a permanent magnet or the like may be used. In FIG. 2, a magnetic flux B is formed in the direction indicated by an arrow Z, and the figure shows that the direction thereof is perpendicular to the surface of the semiconductor Hall device. Since the magnetic flux B is concentrated by the magnetic particle 51, the magnetic flux density at the semiconductor Hall device 2 is increased in comparison to a case where the magnetic particle 51 is not present. Further, because the magnetic field is applied from an upper coil, the magnetic flux density increases in accordance with the distance away from the surface of the sensor chip 1. Therefore, floating magnetic molecules 5 that are not bound to the surface of the sensor chip 1 are attracted upward and do not influence the magnetic flux density that is detected by the semiconductor Hall device 2. Since the output voltage of the semiconductor Hall device 2 is in proportion to the magnetic flux density, whether or not the magnetic molecule 5 is bound on the semiconductor Hall device 2 can be determined by means of the output voltage.

When detecting the presence of a plurality of magnetic molecules with one semiconductor Hall device 2, since the incremental amount of the increase in magnetic flux density due to concentration by a magnetic particle is dependent on the number of magnetic particles, the number of magnetic molecules bound on one semiconductor Hall device 2 can also be detected.

In this embodiment a lower coil CD (second magnetic field generation means) is arranged on the backside of the sensor chip 1. The lower coil CD is not provided for the purpose of detecting magnetic molecules, but is provided to generate a magnetic field for bringing magnetic molecules close to the surface of the sensor chip 1. In place of a coil, a permanent magnet or the like maybe used. Upon introduction of magnetic molecules onto the sensor chip 1, a current is passed through the lower coil CD to generate a magnetic field. Magnetic molecules are attracted to the surface of the sensor chip 1 by the magnetic field that is formed such that the magnetic flux density decreases in accordance with an increase in the distance from the surface of the sensor chip 1, and thus the time taken for binding of magnetic particles to the surface of the sensor chip 1 is reduced.

Figure 3A:
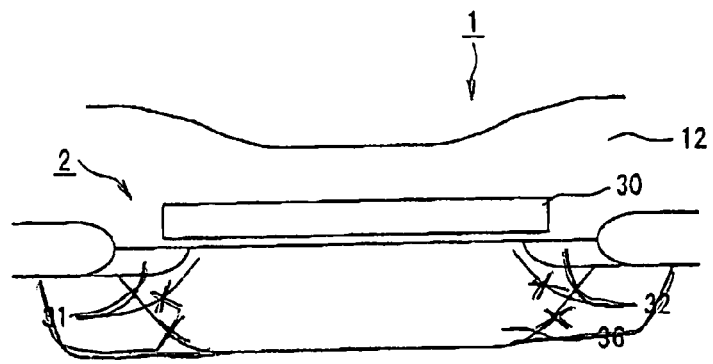
FIG. 3A is a sectional view of a sensor chip.
Figure 3B:
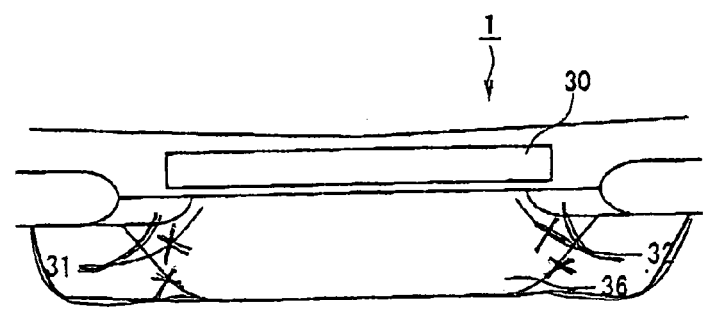
FIGS. 3B and 3C are sectional views of a sensor chip that was subjected to treatment for enhancing the sensitivity of a semiconductor Hall device.
Figure 3C:
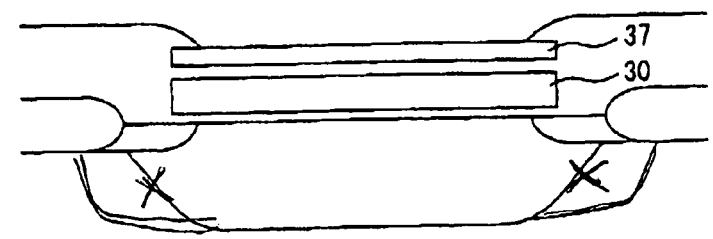

FIGS. 3A to 3C show sectional views of a sensor chip that is subjected to treatment for enhancing the sensitivity of a semiconductor Hall device. The sensor chip 1 is formed by CMOS processes as described above, in which the distance from the gate electrode 30 to the chip surface is normally several μm. A sensing surface of the semiconductor Hall device with respect to magnetic flux is formed in the interface between the gate electrode 30 and a p-well region 36. Because the sensitivity of a semiconductor Hall device with respect to a magnetic molecule is in inverse proportion to the distance thereof from the sensing surface, it is preferable that the thickness of an insulating layer 12 formed on the gate electrode 30 be thin.

Accordingly, after the sensor chip 1 is produced by standard CMOS processes, as shown in FIG. 3B, the insulating layer 12 is removed by etching to a degree such that only the Hall device region is not exposed by the gate electrode 30. Further, as shown in FIG. 3C, a metal layer 37 comprising aluminium or the like may be provided beforehand on the gate electrode 30 as an etching stop layer.

FIG. 2 shows a magnetic molecule 5 that is used in a method for measuring an object to be measured using a biosensor that assays an object to be measured by detecting a magnetic field produced by a magnetic molecule. In this method, a molecule that binds specifically to the object to be measured 62 is used as the magnetic molecule 5, the amount of the magnetic molecule 5 binding specifically to the object to be measured 62 is determined using a biosensor, and the amount of the object to be measured 62 is determined based on the amount of the magnetic molecule 5. However, the biosensor of the present invention is not limited to use only when measuring an object to be measured by detecting a magnetic molecule in this manner. For example, as the magnetic molecule, a molecule may be used that is labeled with a magnetic particle and binds with the surface of a magnetic sensor in competition with an object to be measured. In this case, the amount of magnetic molecules binding to the surface in place of the object to be measured can be determined using a biosensor, and the amount of the competing object to be measured can be determined based on the amount of the magnetic molecule.

The configuration of the semiconductor Hall device of the present invention will be described referring to FIGS. 4A to 4C.

Figure 4A:
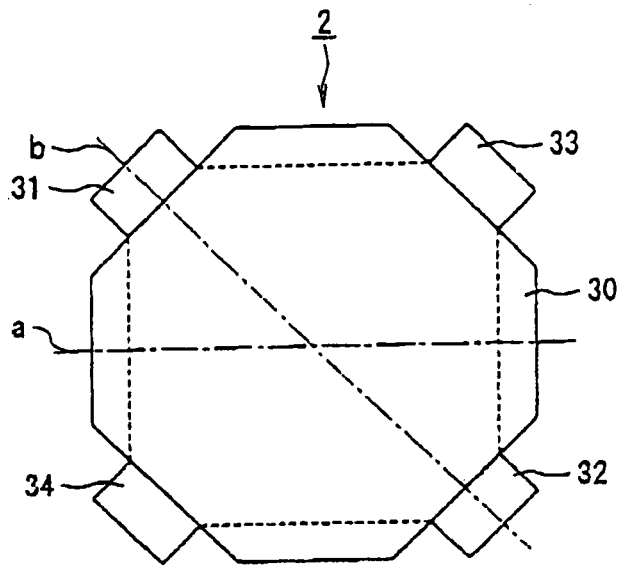
FIG. 4A is a view showing the configuration of a semiconductor Hall device according to the present invention.
Figure 4B:
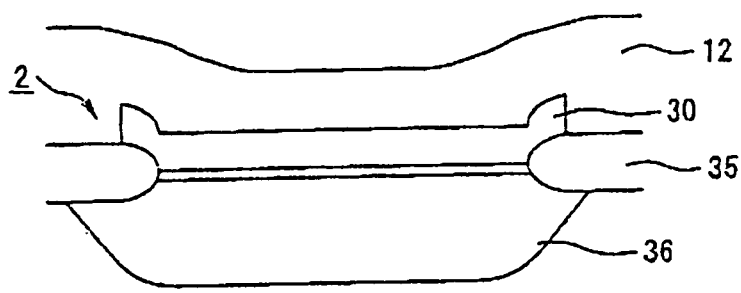
FIG. 4B is a sectional view along an alternate long and short dash line denoted by the reference character "a" in FIG. 4A.
Figure 4C:
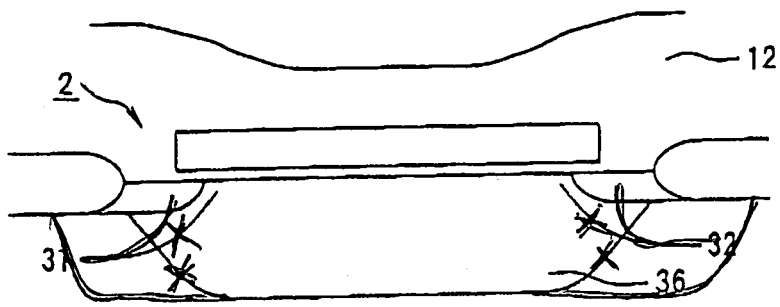
FIG. 4C is a sectional view along an alternate long and short dash line denoted by the reference character "b" in FIG. 4A.

FIG. 4A shows a top view of the semiconductor Hall device 2, FIG. 4B shows a sectional view along the alternate long and short dash line denoted by the reference character "a" in FIG. 4A, and FIG. 4C shows a sectional view along the alternate long and short dash line denoted by the reference character "b" in FIG. 4A. The composition of the semiconductor Hall device 2 includes the gate electrode 30, a source electrode 31, a drain electrode 32, output electrodes 33 and 34, and an insulating layer 35. The semiconductor Hall device 2 is formed in the p-well region 36. The configuration is the same as that of an n-type MOSFET with the exception of the output electrodes. Metal wires to the respective electrodes have been omitted from the figure. The output electrodes 33 and 34 are configured such that current flows perpendicularly to magnetic flux formed roughly perpendicularly to the surface of the sensor chip and current flowing between the source and drain electrodes.

The operation of the semiconductor Hall device 2 is described hereafter. Bias is applied to the gate electrode 30, the source electrode 31 and the drain electrode 32, to set the semiconductor Hall device 2 in the same operating state as a MOSFET. Preferably, at this time, the device operates in a linear region. When an externally applied magnetic flux is not present in this state, the two output electrodes 33 and 34 are at the same potential. When a magnetic flux that is perpendicular to the surface of the semiconductor Hall device is applied from outside, a voltage that is proportionate to the magnetic flux density arises as a differential voltage between the output electrodes 33 and 34.

Figure 5:
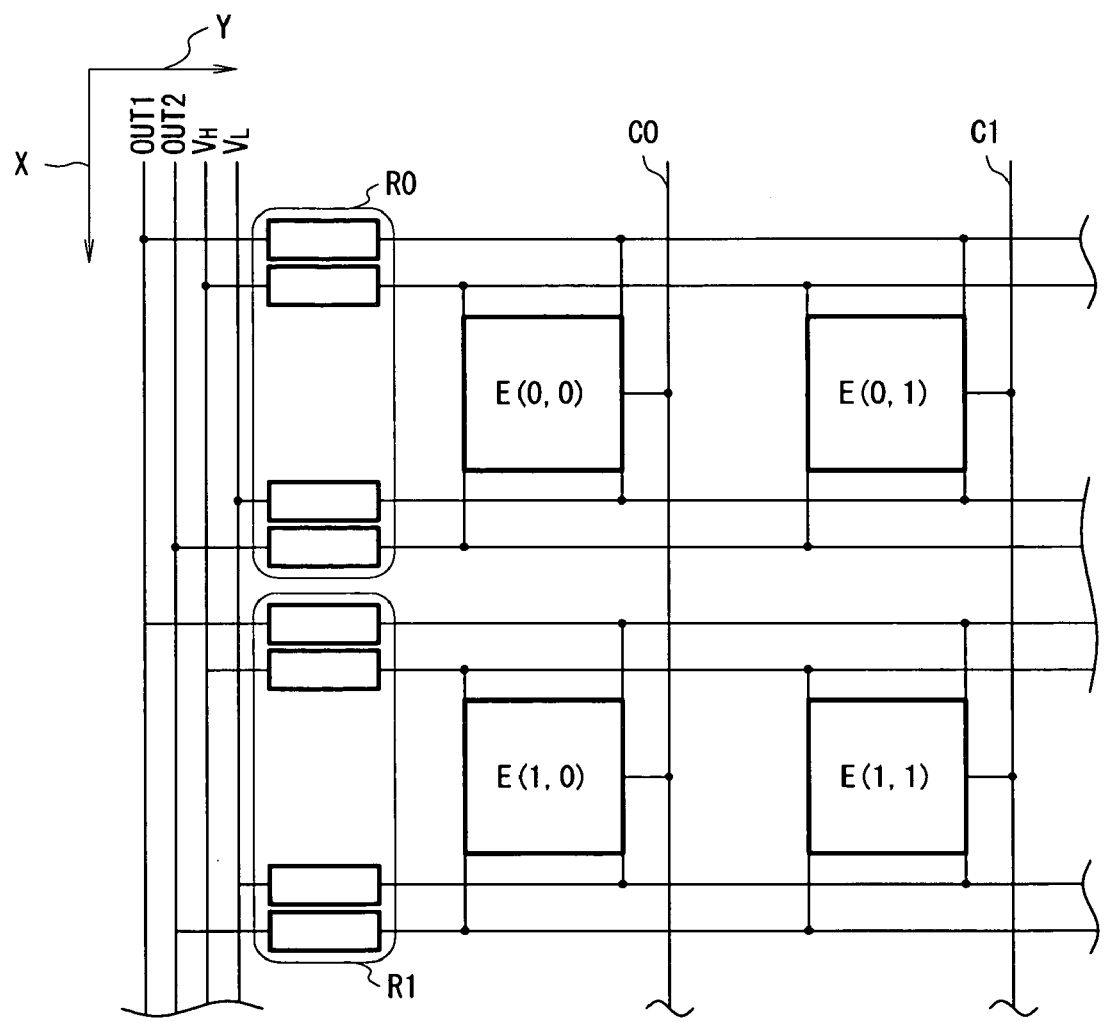
FIG. 5 is a view illustrating a method for selecting Hall devices in an array according to the present invention.

Next, referring to FIG. 5, a method will be described for selecting individual semiconductor Hall devices that are arranged in an array and extracting the output thereof.

A source electrode, drain electrode and pair of output electrodes of individual Hall devices (E(0,0), E(0,1) . . . ) are connected to $V_L$, $V_H$, OUT 1 and OUT 2 via switches (R0, R1 . . . ), and are connected commonly to the same column in the column direction Y. The gate electrodes of the same row in the row direction X are also common, and are connected to the common gate electrode wire C0, C1 . . . of each column. $V_L$ and $V_H$ are wires for supplying bias to the Hall device and OUT 1 and OUT 2 are wires for sending output from the Hall devices to the amplification circuit.

The case of selecting the Hall device E(0,0) will now be described. Only the switch R0 is turned ON, and switches R1, R2 . . . are turned OFF. Further, only the gate electrode line C0 is set to a voltage whereby the Hall device enters an operating state, and the gate electrode lines C1, C2 . . . are set to a voltage whereby the Hall devices do not operate, i.e. to a state whereby a current does not flow between the source and drain electrodes even if a bias is applied to the source electrode and the drain electrode.

At this point, $V_L$ and $V_H$ are applied to the source electrode and drain electrode of the Hall device E(0,0) and the Hall devices in the same row, however current flows only through the Hall device E(0,0). A voltage that is proportionate to the magnetic flux density arises in the output electrodes of the Hall device E (0,0). Because the output electrodes of the Hall devices arrayed in the same row as the Hall device E(0, 0) are not in an operating state, the output voltage of the Hall device E(0,0) is output as it is to OUT 1 and OUT 2. With this configuration, even if the number of arrays increases the number of wires within an array will be the same and it will be only necessary to add a switch to the end. Thus, the area of the sensor chip will be roughly in proportion to the number of arrays, thereby enabling easy configuration of a sensor chip comprising a large number of Hall devices.

Figure 6:
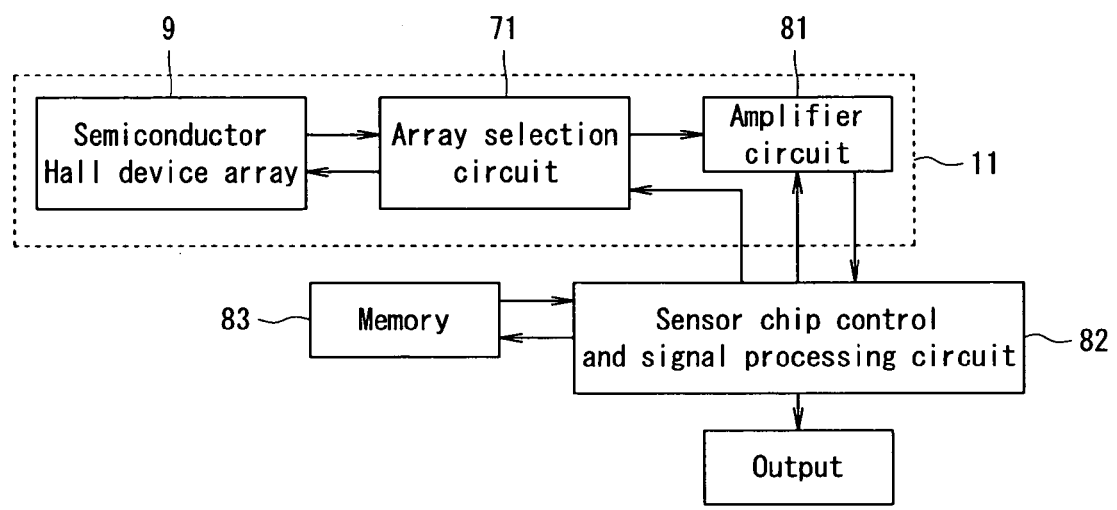
FIG. 6 is a block diagram illustrating a circuit of a biosensor according to the present invention.

FIG. 6 shows the configuration for an entire biosensor. The composition of the biosensor includes the sensor chip 1 for introducing a sample solution and carrying out measurement, and a measurement apparatus main unit that exchanges signals with the sensor chip 1. A semiconductor Hall device array 9, an array selection circuit 71 and an amplification circuit 81 are provided on the sensor chip 1. Other control circuits 82 such as, for example, a sensor chip control circuit to control the sensor chip and a signal processing circuit that processes an output signal from the Hall devices, are provided on the side of the measurement apparatus main unit. The sensor chip 1 may be replaced with a new sensor chip after each measurement.

Next, the circuit operation of the entire biosensor according to the present invention will be described using the flowchart in FIG. 7 while referring to FIG. 6.

In a step S101, in a state where molecular receptors, objects to be measured, and magnetic molecules including magnetic particles have been introduced onto a sensor chip, a magnetic field is applied from a lower coil. The magnetic molecules are attracted to the surface of the sensor chip by the magnetic field that is produced such that the magnetic flux density decreases as the distance from the surface of the sensor chip increases, thereby enhancing the speed of binding to the surface of the sensor chip.

In a step S102, in a state where binding of magnetic molecules to the surface of the sensor chip is completed, the magnetic field originating from the lower coil is turned OFF.

In a step S103, in a state where a magnetic field is not applied to the sensor chip, the output of Hall devices is obtained. Specifically, an address signal for selecting a specific Hall device is sent from a sensor chip control circuit 82 in the measurement apparatus main unit to the array selection circuit 71 on the sensor chip. Based on this address signal the array selection circuit 71 selects the specified Hall device as described above. An output signal from that Hall device is amplified by the amplification circuit 81 on the sensor chip, and stored in a memory 83 as an offset value (first output value).

In a step S104, the sensor chip control circuit judges whether signals have been acquired from all the Hall devices, from which output signals are required, and if all the signals have not been acquired it returns to the step S103. Thus, the output signals of all of the Hall devices are extracted and recorded.

In a step S105, a magnetic field is applied from an upper coil.

In a step S106, as described above, address information of a Hall device is sent to the sensor chip from the sensor chip control circuit 82, an output signal is extracted, and similarly to the step S103, the signal is stored as the output value of the Hall device (second output value) in the memory 83.

In a step S107, as described above, the sensor chip control circuit judges whether signals have been acquired from all the Hall devices, from which output signals are required, and if all the signals have not been acquired it returns to the step S106. Thus, the binding state of magnetic molecules with respect to all the Hall devices is acquired.

In a step S108, the magnetic field of the upper coil is turned OFF.

In a step S109, the offset values of the respective Hall devices acquired in the step S103 and the corresponding output values of the Hall devices acquired in the step S106 are retrieved from the memory 83, and the output values of the Hall devices are corrected using the offset values in the signal processing circuit 82.

In a step S110, the output values after correction in the step S109 are compared with respect to adjacent Hall devices. If the states of adjacent Hall devices are the same, that is, both have magnetic molecules bound thereto or neither has a magnetic molecule bound thereto, the output values will be the same. When the states of adjacent Hall devices are different, that is, only one of the Hall devices has a magnetic molecule bound thereto, the output value of the Hall device having a magnetic molecule bound thereto will be larger than that of the Hall device not having a magnetic molecule bound thereto. This is because the magnetic flux is concentrated by the magnetic molecule.

By comparing the output value of each of the Hall devices with respect to the output value of the Hall device adjacent thereto, the boundaries between regions in which magnetic molecules are bound and regions in which magnetic molecules are not bound can be determined. Thus, it is possible to determine the number of magnetic molecules bound on the sensor chip surface. The above comparison is not limited to comparison between output values of adjacent semiconductor Hall devices, and any comparison may be performed as long as the output values used for comparison are those obtained from semiconductor Hall devices provided in mutually different regions.

Further, a specified Hall device that does not comprise on its surface molecular receptors that capture objects to be measured may be provided as a reference region to which magnetic molecules do not bind.

Figure 7:
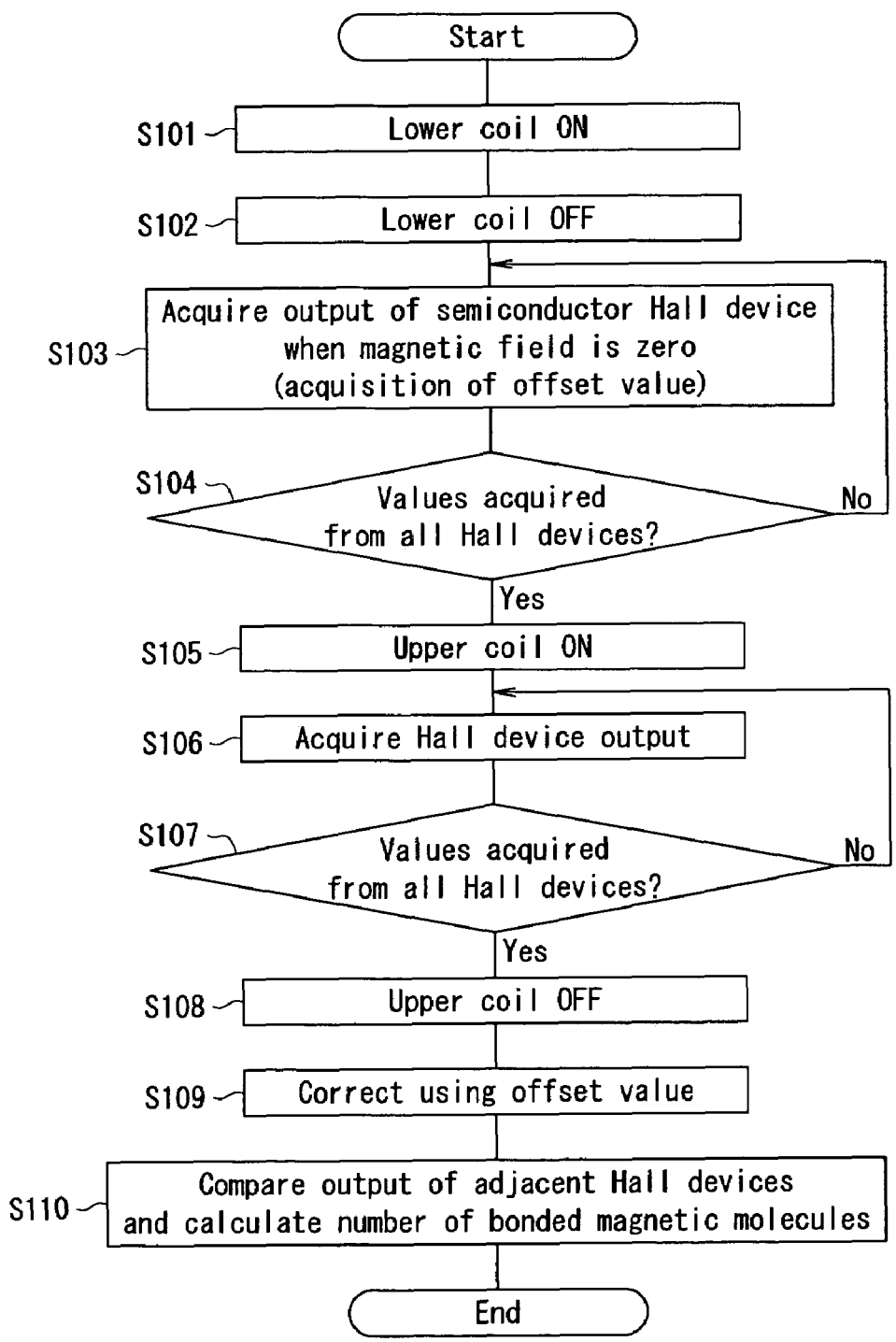
FIG. 7 is a flowchart illustrating the circuit operation of the entire biosensor according to the first embodiment herein.

In FIG. 7, after acquiring the offset values of all the Hall devices, the upper coil is turned ON and the output values of all the Hall devices are then acquired, however it is also possible to acquire the offset value and then acquire the output value for each Hall device, respectively. That is, after executing the step S103 for one Hall device, the steps S105, S106 and S108 are then executed in that order, and after repeating this procedure for each of the Hall devices, the steps S109 and S110 are executed.

The biosensor is controlled using a program for implementing the operations of FIG. 7 as described above. More specifically, the program is a program for controlling a biosensor which includes a measurement step for acquiring the intensities of magnetic fields applied respectively to different regions on the surface of a magnetic sensor, and a determination step for determining the amount of bound magnetic molecules by comparing the intensities of the magnetic fields applied respectively to the mutually different regions that were acquired in the measurement step.

In the measurement step, each of the individual detector elements arranged in a two-dimensional array is selected, and the intensity of the magnetic field detected by each individual detector element is acquired.

It is preferable that the program further comprises an offset value acquisition step for acquiring the outputs from the above detector elements as offset values before a magnetic field is applied to the surface of the magnetic sensor in the above measurement step, and that in the above determination step, comparison is conducted using a value obtained by removing the offset values acquired in the offset value acquisition step from the values acquired from the detector elements in the measurement step.

Also, it is preferable that the program further comprises a binding acceleration step for generating, upon introduction of the magnetic molecules to the surface of the magnetic sensor, a magnetic field for bringing magnetic molecules close to the surface of the magnetic sensor by a magnetic field generation means provided below the surface of the magnetic sensor to which the magnetic molecules bind, and that the speed of binding of the magnetic molecules in the binding acceleration step is enhanced by a magnetic field produced such that the magnetic flux density decreases according to an increase in the distance from the surface of the magnetic sensor.

The biosensor control program can be used by recording the program in the aforementioned memory provided in the measurement apparatus main unit of the biosensor or in a read-only storage device provided in the measurement apparatus main unit, or by storing the program in a storage device of another computer or the like.

Embodiment 2

Next, the circuit operation of the entire biosensor according to the second embodiment of the present invention will be described using the flowchart shown in FIG. 8. The configuration of the entire biosensor is the same as that shown in FIG. 6. However, the amplification circuit 81 in FIG. 6 further comprises a detector circuit for extracting only a frequency component from the output signals of the semiconductor Hall devices.

In a step S201, in a state where objects to be measured and magnetic molecules that include magnetic particles have been introduced onto a sensor chip, a magnetic field is generated by passing a direct current through a lower coil, whereby the magnetic molecules are attracted to the sensor chip surface.

In a step S202, the magnetic field originating from the lower coil is turned OFF.

In a step S203, a magnetic field is generated by passing a direct current through an upper coil, whereby magnetic molecules are attracted away from the sensor chip surface.

In a step S204, the magnetic field originating from the upper coil is turned OFF.

In a step S205, the operation returns to the step S201 and the steps from S201 to S204 are repeated until the lapse of a pre-established time for completion of binding of magnetic molecules to the sensor chip surface or the completion of a pre-established number of step repetitions.

In a step S206, an alternating current magnetic field is generated by passing an alternating current through the upper coil.

In a step S207, the output signal of each Hall device is acquired. Specifically, an address signal for selecting a specific Hall device is sent from the sensor chip control circuit 82 that is provided on the measurement apparatus main unit side to the array selection circuit 71 provided on the sensor chip. Based on this address signal the array selection circuit 71 selects the specified Hall device as described above. The amplification circuit 81 on the sensor chip amplifies the output signal from the Hall device. As described above, the amplification circuit 81 comprises a detector circuit for extracting only a frequency component corresponding to the frequency of the applied magnetic field from the output signal. The output signal extracted by the detector circuit is stored in the memory 83 after amplification.

In a step S208, as described above, judgment is made as to whether signals have been acquired from all of the Hall devices, from which output signals should be acquired. If a signal has not been acquired from all of the Hall devices the operation returns to the step S207. Thus, the output signal of each Hall device is acquired.

In a step S209, the magnetic field of the upper coil is turned OFF.

In a step S210, the output value of each Hall device that was acquired in the step S207 is retrieved from the memory 83 and compared with the output value of the Hall device adjacent thereto in the signal processing circuit 82. If the states of adjacent Hall devices are the same, that is, both have magnetic molecules bound thereto or neither has a magnetic molecule bound thereto, the output values will be the same. When the states of adjacent Hall devices are different, that is, only one of the Hall devices has a magnetic molecule bound thereto, the output value of the Hall device having a magnetic molecule bound thereto will be larger than the output value of the Hall device not having a magnetic molecule bound thereto. This is because the magnetic flux is concentrated by the magnetic molecule, thus causing an increase in the output value of the Hall device having a magnetic molecule bound thereto.

By comparing the output value of each Hall device with the output value of the Hall device adjacent thereto, the boundaries between regions in which magnetic molecules are bound and regions in which magnetic molecules are not bound can be determined. Thus, it is possible to determine the number of magnetic molecules bound on the sensor chip surface.

Figure 8:
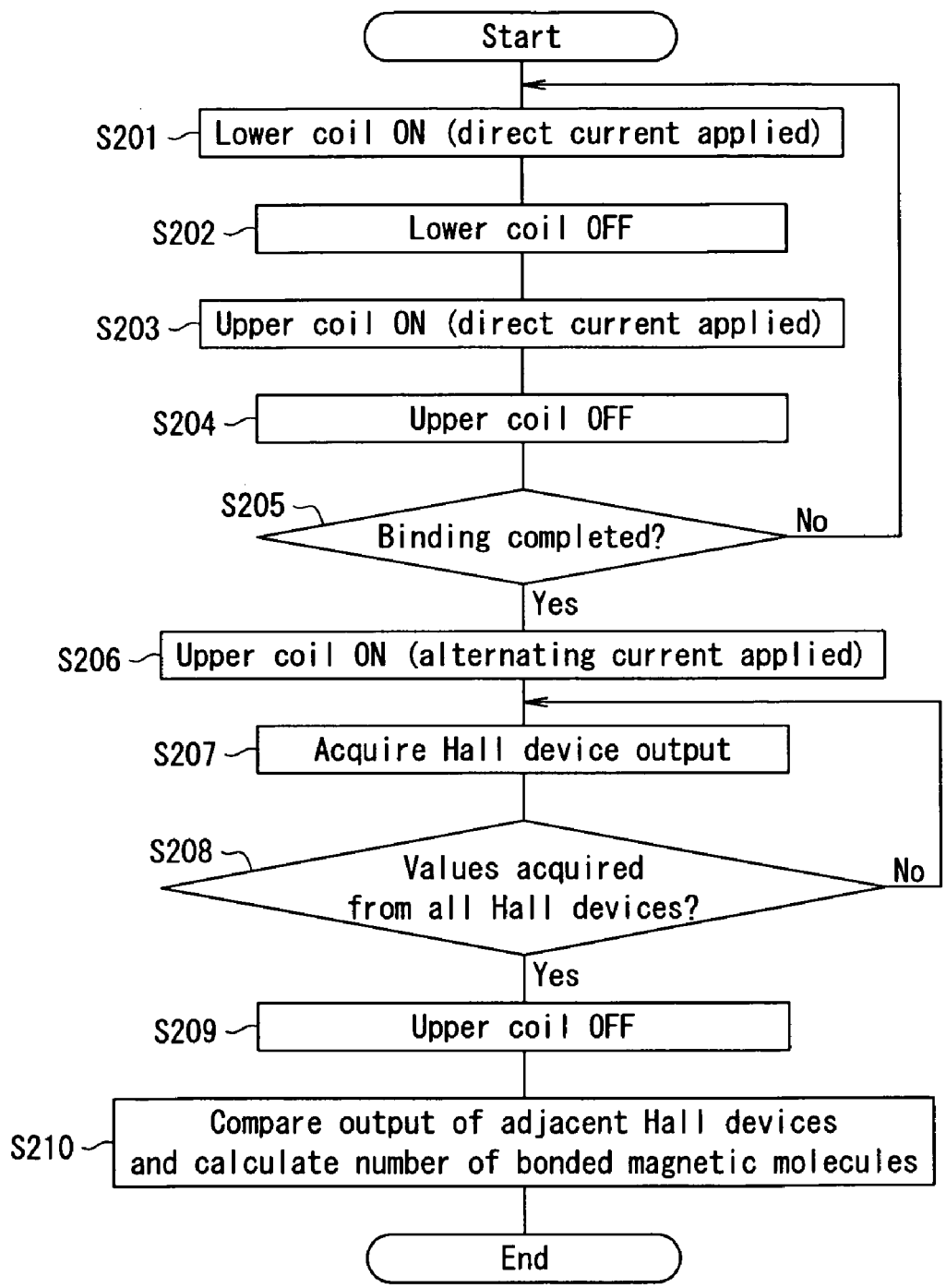
FIG. 8 is a flowchart illustrating the circuit operation of the entire biosensor according to the second embodiment herein.

The biosensor is controlled using a program for implementing the operations of FIG. 8 as described above. More specifically, the program is a program for controlling the aforementioned biosensor in which, in the above measurement step, by means of a magnetic field applied at a constant frequency to the sensor surface, an output signal of a detector element is obtained that includes a signal output at a frequency corresponding to the magnetic field; and in the above determination step, using a magnetic field applied at a constant frequency across the above magnetic sensor, by retrieving only a frequency component corresponding to the magnetic field from an output signal of a detector element that includes a signal output at a frequency corresponding to the magnetic field, an offset signal included as a direct current component can be removed from the output signal.

That is, the output signal of the detector element comprises an alternating current signal that corresponds to the frequency of an applied alternating current magnetic field and a direct current offset signal that is output regardless of the application of a magnetic field. By means of the detector circuit, an offset value included as a direct current component in the output signal of a detector element can be eliminated by acquiring only a frequency component for an applied alternating current magnetic field from the output signal of the detector element.

It is preferable that the program further comprises a stirring step to be conducted after the introduction of the magnetic molecules to the surface of the magnetic sensor and prior to the above measurement step. In the stirring step, magnetic molecules are stirred by alternately producing magnetic fields by means of a first magnetic field generation means provided in a position facing the surface of the magnetic sensor and a second magnetic field generation means provided below the surface of the magnetic sensor.

Preferably, in the above stirring step, by alternately inverting the inclination of the magnetic flux density formed in a perpendicular direction to the surface of the magnetic sensor, the speed of binding between an object to be measured and a magnetic molecule is enhanced, and the speed of binding between a molecular receptor immobilized on the surface of the magnetic sensor and a magnetic molecule bound with an object to be measured is also enhanced.

With respect to the description of the scope of the claims, the present invention may take the following form.

(1) The biosensor according to claim 13, which further comprises a magnetic field switching means for performing switching such that the first magnetic field generation means and the second magnetic field generation means alternately generate a magnetic field, characterized in that magnetic molecules are stirred by alternately changing a state of distribution of a magnetic field on a magnetic sensor surface by means of the magnetic field switching means.

Thereby, magnetic particles can be stirred in a sample solution, and the speed of binding between magnetic particles used as labels in measurement and other substances can be enhanced, and thus a time required for measurement can be reduced.

As used herein, a magnetic field switching means may be composed of, for example, a switch for alternately passing current to a first coil used as a first magnetic field generation means and a second coil used as a second magnetic field generation means. The switching frequency and switching time and the like may be set up in advance.

Embodiment 3

Figure 9:
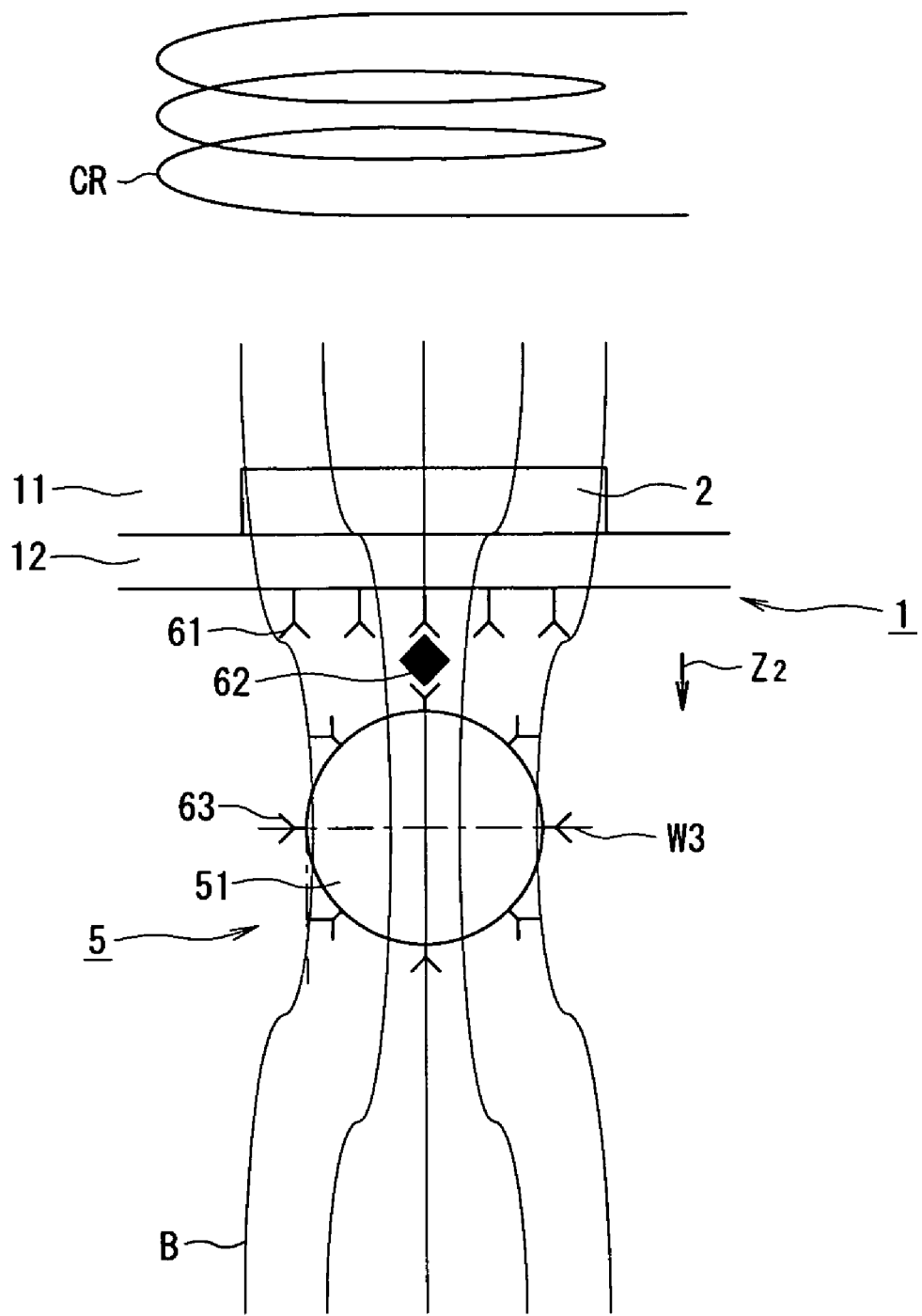
FIG. 9 is a view illustrating the detection principles of the biosensor according to the third embodiment herein.

Next, the detection principles of a biosensor according to the third embodiment of the present invention will be described using FIG. 9. FIG. 9 is a view schematically showing a cross section of the vicinity of the semiconductor Hall device 2 of the sensor chip 1. The molecular receptors 61 composed of antibodies are immobilized on the surface of the semiconductor Hall device 2. The object to be measured 62 is bound specifically to one of the molecular receptors 61. Further, the magnetic particle 51 is bound to the object to be measured 62 through specific binding between the object to be measured 62 and one of the molecular receptors 63 that are composed of antibodies. The magnetic particle 51 and the molecular receptors 63 bind to each other to form the magnetic molecule 5.

The sensor chip 1 is arranged with its surface facing downward, and a rear coil CR (second magnetic field generation means) is provided. The intensity of a magnetic field generated by the rear coil CR is set such that the intensity is sufficient for attracting magnetic molecules to the surface of the sensor chip 1. As shown in FIG. 9, part of a magnetic molecules binds to the surface of the sensor chip 1. In this state, the magnetic field generated by the rear coil CR is weakened to a degree such that floating magnetic molecules that are not bound to the surface of the sensor chip 1 sink downward due to gravitational force.

In FIG. 9, the magnetic flux B is formed in the direction shown by an arrow Z2, which is perpendicular with respect to the surface of the semiconductor Hall device. Since the magnetic flux B is concentrated at the magnetic particle 51, the magnetic flux density at the semiconductor Hall device 2 is increased in comparison to a case where the magnetic particle 51 is not present. At this point, magnetic molecules 5 that have sunken downward do not affect the magnetic flux density detected by the semiconductor Hall device 2. Since the output voltage of the semiconductor Hall device 2 is in proportion to the magnetic flux density, whether or not a magnetic molecule 5 is bound on the semiconductor Hall device 2 can be determined based on the output voltage.

In this embodiment it is preferable that at the time of introduction of magnetic molecules to the sensor chip 1, the rear coil CR intermittently generates a magnetic field of an intensity sufficient for attracting magnetic molecules to the surface of the sensor chip 1, such that the speed of binding between objects to be measured and magnetic particles is enhanced by stirring in which the magnetic particles are moved up and down, and further, the speed of binding of magnetic particles bound with objects to be measured to molecular receptors that are immobilized on the magnetic sensor surface is also enhanced.

Figure 10:
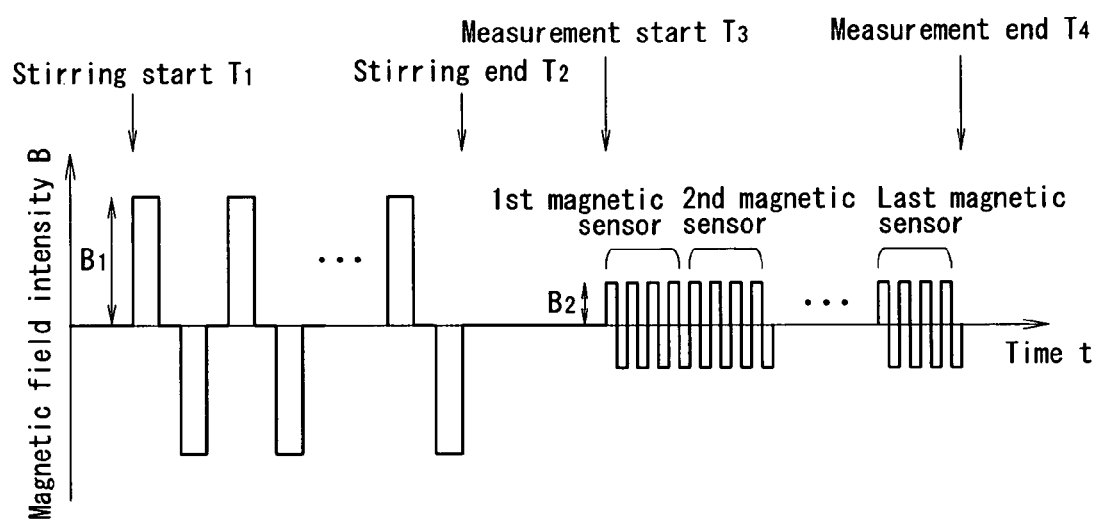
FIG. 10 is a view illustrating the states of a magnetic field applied to magnetic molecules by a coil in the third embodiment herein.

The state of a magnetic field applied to magnetic molecules by the coil according to Embodiment 3 is shown in FIG. 10.

First, magnetic molecules are stirred to facilitate reaction between molecular receptors and objects to be measured. During the period from stirring start $T_1$ to stirring end $T_2$, the rear coil CR intermittently applies a magnetic field having a magnetic field intensity $B_1$ that is strong enough to attract magnetic molecules. In the figure, the generated magnetic field is bipolar, however the magnetic field may be unipolar.

After completion of reaction, in a measurement step (from measurement start $T_3$ to measurement end $T_4$) the rear coil CR generates a weak alternating current magnetic field of a magnetic field intensity $B_2$ that is of an intensity such that the magnetization of magnetic molecules does not become saturated, and the signals of all magnetic sensors are measured.

Next, the circuit operation of the entire biosensor according to Embodiment 3 of the present invention will be explained using the flowchart in FIG. 11. The configuration of the entire biosensor is the same as that shown in FIG. 6, except that the amplification circuit 81 in FIG. 6 further comprises a detector circuit for extracting only a frequency component from the output signal of a semiconductor Hall device.

In a step S301, in a state where objects to be measured and magnetic molecules that include magnetic particles have been introduced to a sensor chip, a magnetic field is generated bypassing intermittent current through the rear coil, whereby magnetic molecules are attracted to the sensor chip surface during periods when the current is flowing.

In a step S302, the operation returns to the step S301 and the steps S301 and S302 are repeated until a pre-established time for completion of binding of magnetic molecules to the sensor chip surface has lapsed.

In a step S303, the magnetic field originating from the rear coil is turned OFF.

In a step S304, an alternating current magnetic field is applied by passing alternating current through the rear coil.

In a step S305, the output signal of each Hall device is acquired. Specifically, an address signal for selecting a specific Hall device is sent from the sensor chip control circuit 82 that is provided on the measurement apparatus main unit side to the array selection circuit 71 provided on the sensor chip. Based on this address signal, the array selection circuit 71 selects the specified Hall device as described above. The output signal from the Hall device in question is amplified by the amplification circuit 81 on the sensor chip. As described above, the amplification circuit 81 comprises a detector circuit for extracting only a frequency component corresponding to the frequency of the applied magnetic field from the output signal. The output signal extracted by the detector circuit is stored in the memory 83 after amplification.

In a step S306, as described above, judgment is made as to whether signals have been acquired from all of the Hall devices, from which output signals should be acquired. If a signal has not been acquired from each of the Hall devices the operation returns to the step S305. Thus, the output signals of all the Hall devices are acquired.

In a step S307, the magnetic field of the rear coil is turned OFF.

In a step S308, the output value for each Hall device that was acquired in the step S305 is retrieved from the memory 83. Then, in the signal processing circuit 82, comparison is carried out between output values of Hall devices that do not comprise molecular receptors on their surface, that is, Hall devices arranged in a reference region, and output values of Hall devices that comprise molecular receptors on their surface. If a Hall device that comprises a molecular receptor on its surface does not have a magnetic molecule binding thereto, the output value thereof will be at the same level as the output value of a Hall device arranged in the reference region. If a Hall device has a magnetic molecule binding thereto, the output value thereof will be larger than that of a Hall device in the reference region since the magnetic flux will be concentrated by the magnetic molecule.

By comparing the respective output values of all the Hall devices having molecular receptors on their surface with the output value of a Hall device that does not have a molecular receptor on its surface, the number of magnetic molecules bound on the sensor chip can be determined.

Figure 12:
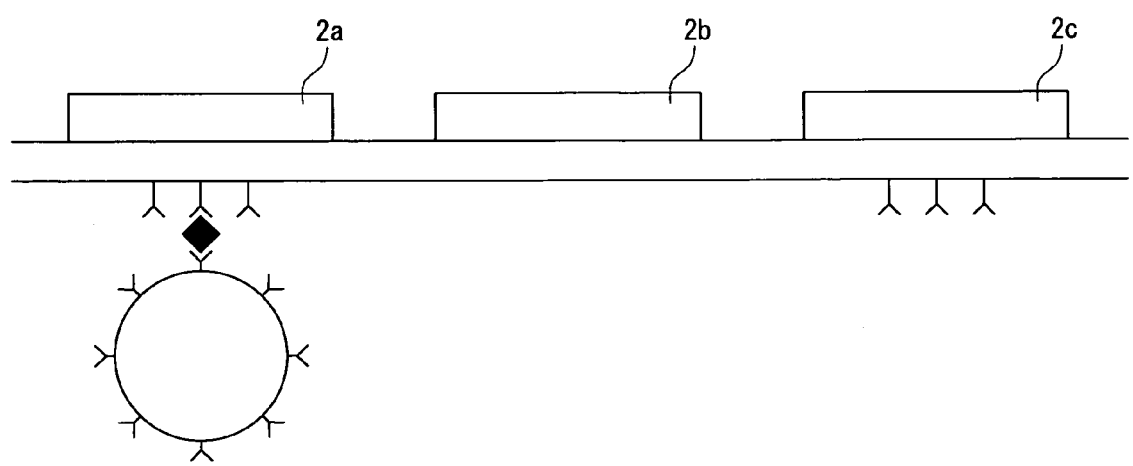
FIG. 12 is a view showing the state of disposition of Hall devices in the third embodiment herein.

FIG. 12 is a view showing the state of disposition of Hall devices in this embodiment.

In the figure, of Hall devices 2a, 2b, and 2c, only the Hall devices 2a and 2c comprise molecular receptors on their surface.

When the size of the Hall voltage, which is the voltage difference between two output terminals of the Hall device, is represented by "VD", and the size of the magnetic flux density of a magnetic field applied to the Hall device is represented by "B", the following formula (1) applies:

$$VD = A \times B \quad \text{Formula (1) (A is a proportionality factor)}$$

When the size of the magnetic flux density of a magnetic field applied to a Hall device by a rear coil in a state where magnetic molecules are not bound to the surface thereof is taken as "B0", and the size of the magnetic flux density in a state where magnetic molecules are bound to the surface thereof is taken as "B0 (1+Δ)", the sizes $VD_{2a}$, $VD_{2b}$, $VD_{2c}$, of the Hall voltage of the respective Hall devices 2a, 2b and 2c are respectively represented in the following formulas (2) to (4):

$$VD_{2a} = A \times B0(1+\Delta) \quad \text{Formula (2)}$$

$$VD_{2b} = A \times B0 \quad \text{Formula (3)}$$

$$VD_{2c} = A \times B0 \quad \text{Formula (4)}$$

When the sensitivity of the Hall device, i.e., "A", is unchanging and the size "B0" of the magnetic flux density of a magnetic field applied to every Hall device or every time of measurement by a coil is also constant, the presence or absence of binding of a magnetic molecule on the surface of each Hall device can be determined from the absolute value of the Hall voltage. However, although in theory the sensitivity and the size of the magnetic flux density applied by a coil will be the same for adjacent Hall devices, because of variations in the production process or variations in the distance between the coil and the Hall devices and the like, the absolute value thereof is not always constant. Therefore, for individual Hall devices it is difficult to determine the presence or absence of binding of a magnetic molecule on the surface thereof using only the Hall voltage thereof.

If the size of the Hall voltage of the Hall device 2b is taken as a reference, and the difference thereof with the Hall voltages of the Hall devices 2a and 2b is calculated, the resulting values will be those shown respectively in formulas (5) and (6).

$$VD_{2a} - VD_{2b} = A \times B0 \times \Delta \quad \text{Formula (5)}$$

$$VD_{2c} - VD_{2b} = 0 \quad \text{Formula (6)}$$

Thus, by employing as a reference the Hall voltage of a Hall device in a reference region, which is a Hall device not comprising a molecular receptor on the surface thereof, even if the absolute value of the magnetic flux density or the sensitivity fluctuates, the presence or absence of binding of a magnetic molecule can be identified based on whether or not the difference is zero.

The difference can also be determined in this way in the comparison to determine the presence or absence of binding. For example, as described hereafter, the presence or absence of binding can also be determined based on a value obtained by dividing the Hall voltage that is the object for comparison by the Hall voltage of a reference region.

As described in the foregoing, a reference region may be provided, for example, by previously providing an unformed region of a gold thin film on a sensor surface. Thereby, at the time of immobilizing molecular receptors, molecular receptors are not immobilized on the reference region, and thus a region to which the magnetic particles 51 are incapable of binding is formed. The number of reference regions on a sensor surface is not limited to one, and a plurality of reference regions may be provided thereon.

Figure 11:
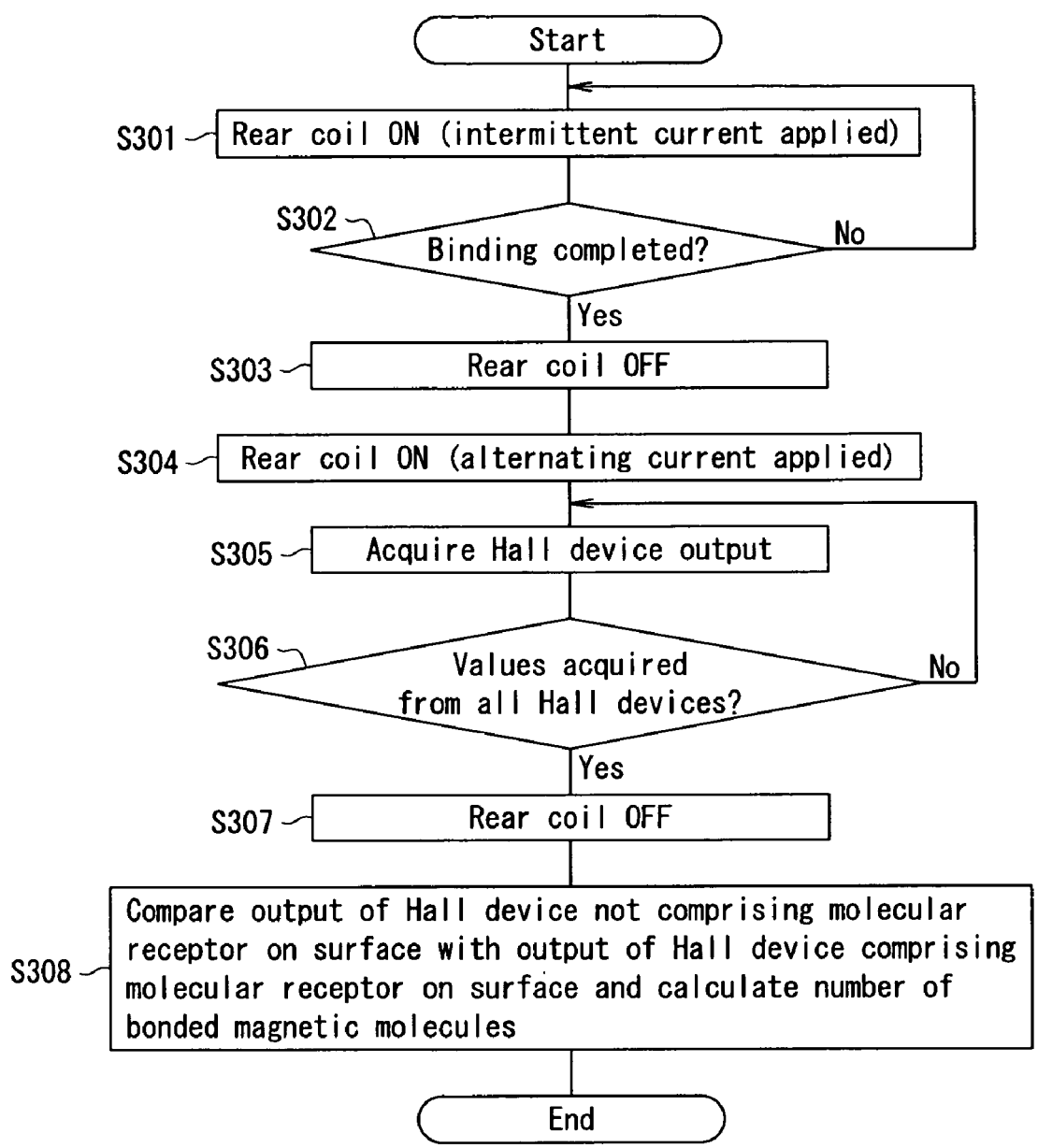
FIG. 11 is a flowchart illustrating the circuit operation of the entire biosensor according to the third embodiment herein.

The biosensor is controlled using a program for implementing the operations in FIG. 11 as described above.

More specifically, the program is a program for controlling the aforementioned biosensor in which, in the above offset value correction step, using a magnetic field applied at a constant frequency across the above magnetic sensor, by retrieving only a frequency component corresponding to the magnetic field from an output signal of a detector element that includes a signal output at a frequency corresponding to the magnetic field, an offset signal included as a direct current component can be removed from the output signal.

That is, the output signal of the detector element comprises an alternating current signal that corresponds to the frequency of an applied alternating current magnetic field and a direct current offset signal that is output regardless of the application of a magnetic field. Using the detector circuit, an offset value included as a direct current component in the output signal of a detector element can be eliminated by acquiring only the component of the frequency of the applied alternating current magnetic field from the output signal of the detector element.

Further, at the time of introduction of the magnetic molecules to the surface of the magnetic sensor, a magnetic field generation means that generates a magnetic field for drawing the magnetic molecules close to the magnetic sensor surface is intermittently activated to enable stirring of the magnetic molecules.

In the aforementioned stirring step, by producing a magnetic flux intermittently in a direction perpendicular to the surface of the magnetic sensor, the speed of binding between objects to be measured and magnetic molecules can be enhanced. Further, the speed at which a magnetic molecule bound with an object to be measured comprising an antigen binds through the object to be measured with a molecular receptor immobilized on the magnetic sensor surface that captures the object to be measured can be enhanced.

Figures 13, 14:
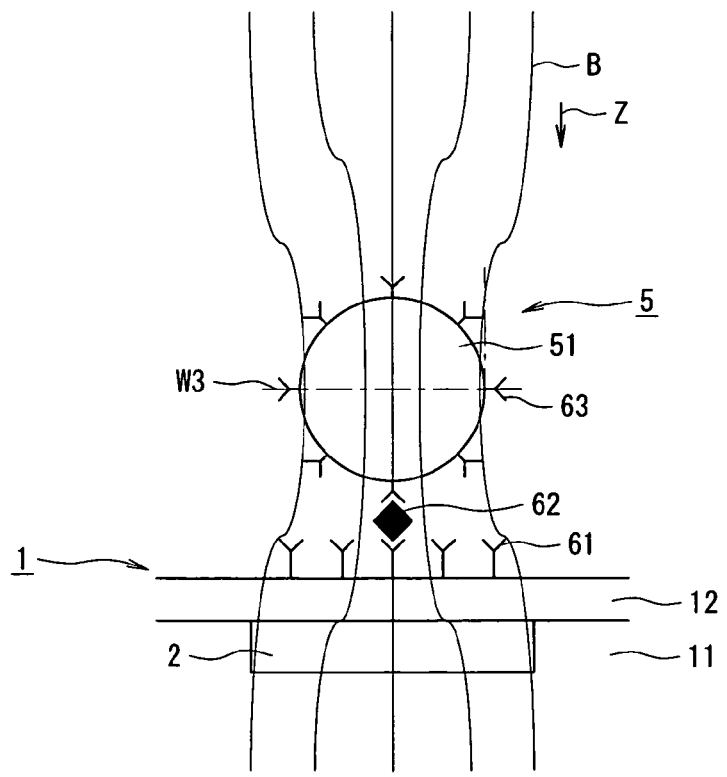
FIG. 13 is a table showing values used for comparison of output values in the third embodiment herein.
FIG. 14 is a view schematically showing a cross section of the sensor chip used in the fourth embodiment herein.

FIG. 13 is a table showing values obtained by dividing the output values of five Hall devices having on their surfaces molecular receptors capturing objects to be measured by the output value of a Hall device not having a molecular receptor on its surface, in which the respective output values were obtained in a measurement step.

In this measurement, Hall devices having the form shown in FIGS. 4A to 4C were arranged in an array, and an array selection circuit and amplification circuit were fabricated on the same silicon substrate. The distance between the source electrode 31 and drain electrode 32 of the Hall device was approximately 6.4 μm, and the distance from the sensing surface, that is, from a channel formed below the gate electrode 30 to the surface of the insulating layer 12, was approximately 2.8 μm. The disposition pitch of the Hall devices arranged in the array was 12.8 μm. A voltage between the source electrode and drain electrode of a Hall device selected by the array selection circuit was approximately 4 V, and a voltage between the source electrode and gate electrode was approximately 5 V. The magnetic flux density generated on the surface of the Hall devices by a coil was 20 Hz, and approximately 50 grms. Magnetic particles manufactured by Dynal Biotech (product name: Dynabeads) having a diameter of 4.5 μm were used as the magnetic particles.

Referring to FIG. 13, the output of semiconductor Hall devices No. 2, No. 4, and No. 5 is approximately 5% larger than the output of a semiconductor Hall device not having a molecular receptor on its surface. Therefore, it could be assumed that magnetic particles were bound to the semiconductor Hall devices No. 2, No. 4, and No. 5. In verification using a microscope it was found that magnetic particles were bound to the surfaces of semiconductor Hall devices No. 2, No. 4, and No. 5, and magnetic particles were not bound to the surfaces of semiconductor Hall devices No. 1 and No. 3. This matched the results shown in FIG. 13.

Embodiment 4

FIG. 14 schematically shows a cross section of a sensor chip used in Embodiment 4.

In FIG. 14, a magnet is arranged above the sensor chip 1. At this point, the magnetic flux B originating from the magnet is formed in the direction shown by the arrow Z that is perpendicular to the surface of the semiconductor Hall device. Because the magnetic flux B is concentrated at the magnetic particle 51, the magnetic flux density at the semiconductor Hall device 2 is increased in comparison to a case where the magnetic particle 51 is not present. Since the output voltage of the semiconductor Hall device 2 is in proportion to the magnetic flux density, it is possible to determine whether or not the magnetic molecule 5 is bound on the semiconductor Hall device 2 based on the output voltage.

Using the flowchart shown in FIG. 15, the circuit operation of the entire biosensor according to Embodiment 4 that uses the biosensor shown in FIG. 14 will be described. The configuration of the entire biosensor used herein is the same as that shown in FIG. 6.

In a step S401, in a state where objects to be measured and magnetic molecules that include magnetic particles are not introduced onto a sensor chip, a magnetic field is applied by a magnet and the intensity of a magnetic field prior to binding of magnetic molecules is acquired. Specifically, an address signal for selecting a specific Hall device is sent from a sensor chip control circuit 82 that is located on the measurement apparatus main unit side to an array selection circuit 71 on the sensor chip. Based on this address signal, the array selection circuit 71 selects the specified Hall device as described above. The output signal from the Hall device in question is amplified by the amplification circuit 81 on the sensor chip, and stored in the memory 83 as an initial value.

In a step S402, judgment is made as to whether signals have been acquired from all the Hall devices, from which output signals should be acquired. If a signal has not been acquired from each Hall device the operation returns to the step S401. Thus, the output signal of each Hall device is extracted and recorded.

In a step S403, objects to be measured and magnetic molecules are introduced onto a sensor chip in a state where a magnetic field is not applied thereto, and upon completion of binding a magnetic field of the same intensity as that in the step S401 is applied by the magnet. In this state, as described above, address information of a Hall device is sent from the sensor chip control circuit 82 to the sensor chip, and the output signal of the relevant Hall device is extracted.

In a step S404, the initial value of the same Hall device that was acquired in the step S401 is retrieved from the memory 83. In the signal processing circuit 82, the output signal extracted in the step S403 and the initial value are compared.

In a step S405, the result of the comparison conducted in the step S404 is output. Since the output of a Hall device to which a magnetic molecule is bound will be different to the initial value thereof, irrespective of the fact that magnetic fields of the same intensity were applied thereto, it is thus possible to determine whether or not a magnetic molecule is bound on a Hall device in an arbitrary position. Also, as described hereafter, by obtaining a comparison result for each of the Hall devices, the number of magnetic molecules bound on the sensor chip can be determined. The comparison results can be output as the number of magnetic molecules bound on a sensor chip or as position information, according to the purpose of use.

In a step S406, as described above, judgment is made as to whether signals have been acquired from all the Hall devices, from which output signals should be acquired. If a signal has not been acquired from each Hall device the operation returns to the step S403. Thus, the state of binding of magnetic molecules on each of the Hall devices is acquired.

Figure 15:
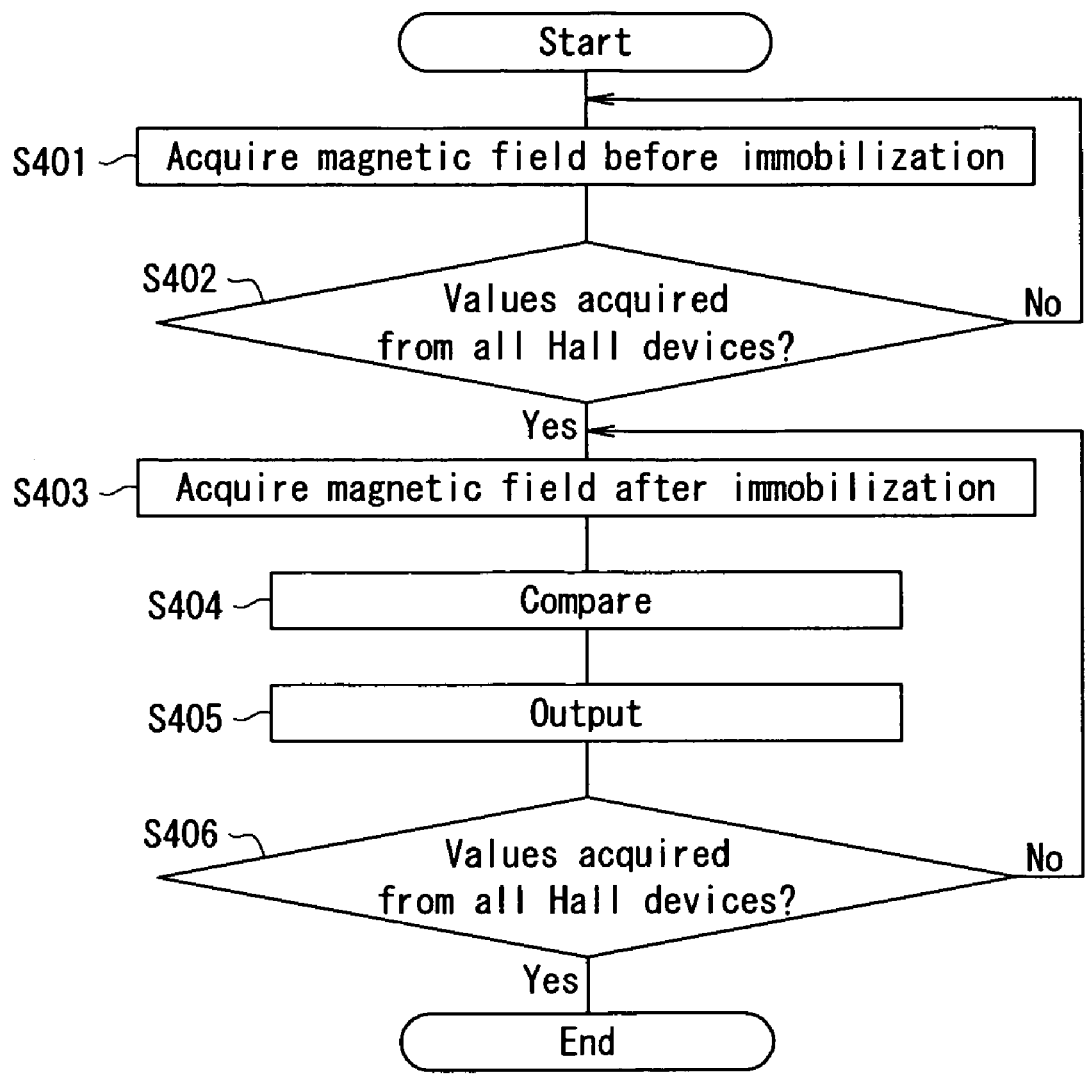
FIG. 15 is a flowchart illustrating the circuit operation of the entire biosensor according to the fourth embodiment herein.

The biosensor is controlled using a program for implementing the operations in FIG. 15 as described above. More specifically, the program is a program for controlling the aforementioned biosensor that includes: a pre-binding measurement step for acquiring the intensity of a magnetic field applied to a magnetic sensor prior to binding of magnetic molecules; a post-binding measurement step for acquiring the intensity of a magnetic field applied to a magnetic sensor after binding of magnetic molecules; and a determination step for determining the amount of bound magnetic molecules by comparing the intensity of the magnetic field prior to binding with the intensity of the magnetic field after binding. Further, in the pre-binding measurement step and the post-binding measurement step, each of the detector elements arranged in a two-dimensional array is selected, and the intensity of the magnetic field detected by each detector element is acquired. The biosensor control program can be used by recording the program in the aforementioned memory provided in the measurement apparatus main unit of the biosensor or in a read-only storage device provided in the measurement apparatus main unit, or by storing the program in a storage device of another computer or the like.

Figures 16, 17:
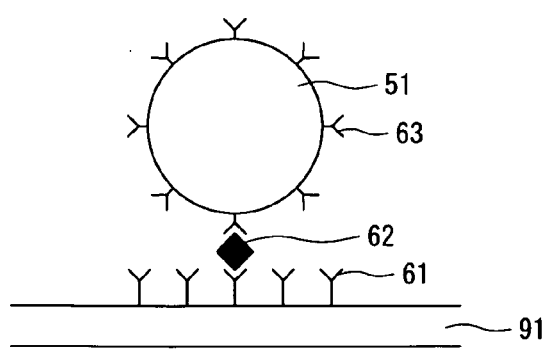
FIG. 16 is a table showing values for output signals prior to binding and output signals after binding.
FIG. 17 is a schematic diagram illustrating a conventional method of solid phase assay using a magnetic particle.

FIG. 16 shows the values for output signals prior to binding and output signals after binding.

In this measurement, Hall devices having the form shown in FIGS. 3A to 3C were arranged in an array and an array selection circuit and amplification circuit were fabricated on the same silicon substrate. The distance between the source electrode 31 and drain electrode 32 of the Hall devices was approximately 6.4 µm, and the distance from the sensing surface, that is, from a channel formed below the gate electrode 30 to the surface of the insulating layer 12 was approximately 5 µm. The disposition pitch of the Hall devices arranged in the array was 12.8 µm. The gain of the amplification circuit was 100-fold. A voltage between the source electrode and the drain electrode of a Hall device selected by the array selection circuit was approximately 4V, and a voltage between the source electrode and the gate electrode was approximately 5 V. The magnet used was such that a magnetic flux density of approximately 2500 gauss was generated across the surface of the Hall device. The magnetic particles used were manufactured by Dynal Biotech (product name: Dynabeads) and had a diameter of 4.5 µm.

FIG. 16 shows the values of output signals from five Hall devices arranged in an array, before and after binding of magnetic molecules. Referring to FIG. 16, for semiconductor Hall devices No. 1 to No. 5 arranged in an array at respectively different positions, a pre-binding output voltage (mV), a post-binding output voltage (mV) and a voltage difference (mV) between the two are, respectively, (882, 882, 0) for semiconductor Hall device No. 1; (886, 887, 1) for semiconductor Hall device No. 2; (885, 885, 0) for semiconductor Hall device No. 3; (887, 892, 5) for semiconductor Hall device No. 4; and (886, 887, 1) for semiconductor Hall device No. 5. As is clear from the differences between the values for pre-binding and post-binding, the signal from semiconductor Hall device No. 4 to which magnetic molecules attached was the only signal that increased. Therefore it could be assumed that magnetic molecules bound only to the semiconductor Hall device No. 4. In confirmation using a microscope prior to binding and after binding on the Hall devices, it was found that magnetic molecules bound only to semiconductor Hall device No. 4, and magnetic molecules did not bind to any of the other semiconductor Hall devices. This matched the results for the output signals.

The above description relates to specific embodiments of the present invention. A person skilled in the art can suitably devise various modifications of the present invention, and such modifications are also encompassed in the technical scope of the present invention.

INDUSTRIAL APPLICABILITY

By using the biosensor according to the present invention, it is possible to determine the two-dimensional distribution of objects to be measured or the amount of bound objects to be measured.

In particular, by determining the amount of an object to be measured by comparing the intensities of magnetic fields of respectively different regions on the surface of a magnetic sensor, measurement can be performed promptly. This is because the value of a magnetic field to be the object for comparison and the value of a magnetic field to be the reference for comparison can be acquired in the same state, that is, in a state where magnetic molecules and objects to be measured have been introduced onto the magnetic sensor. Further, by obtaining an output value in a reference region to which magnetic molecules cannot bind and comparing that value with the output value of each detector element, precise assessment of the presence or absence of binding is enabled irrespective of fluctuations in the sensitivity of the sensor or fluctuations in the absolute value of the magnetic flux density or the like, and detection of minute changes in a magnetic field is also enabled. In addition, with respect to offset values that depend on the configuration of a sensor, values can be acquired having conditions of a sample solution in which magnetic molecules or the like are introduced and operating conditions of an apparatus and the like equivalent to those at the time of measurement, whereby measurement of a higher accuracy is possible.

By making the size of the surface of semiconductor Hall devices equivalent to or less than the size of magnetic molecules and making the intervals at which the semiconductor Hall devices are arranged larger than the size of the magnetic particles, interference from other magnetic molecules can be eliminated. This can enhance the accuracy of detection and analysis.

Further, by selectively immobilizing molecular receptors on the surface of a magnetic sensor, for example, by immobilizing molecular receptors on sections corresponding to the sites of semiconductor Hall devices, the detection state of magnetic molecules binding to molecular receptors can be adjusted.

Forming a magnetic sensor using semiconductor Hall devices according to the present invention makes it possible to use common interconnections, and thus the number of devices can be easily increased and construction of a low-cost, small-size biosensor is enabled.

Further, by attracting magnetic molecules that are not bound to a sensor surface away from the sensor surface utilizing a magnetic field, it is possible to carry out fast and accurate measurement without the need to wash away floating magnetic molecules that have not bound to the magnetic sensor surface when determining the quantity of bound magnetic molecules.

While measurement may be conducted after removing unbound magnetic molecules using a magnet or the like, constructing a biosensor in which the sensor surface is facing downward allows measurement to be performed at the same time as isolation of unbound molecules. In addition, it also allows the intensity of a magnetic field to be applied at the time of measurement to be kept to a level whereby the magnetic field does not become saturated, thereby enabling output signals to be obtained from Hall devices to be more obvious.

By providing a magnetic field generation means that attracts magnetic molecules to the surface of the magnetic sensor, it is possible to speed up binding of magnetic molecules to the magnetic sensor surface, thereby reducing the assay time.

Further, by forming a magnetic sensor, selection means, and signal amplification circuit on one chip, it is possible to miniaturize the magnetic sensor and, at the same time, to replace one magnetic sensor with another according to a sample solution used.

The invention claimed is:

1. A biosensor for analyzing material containing measurement objects by measuring magnetic molecules having first molecular receptors bound to the measurement objects, comprising:
   a magnetic sensor having a surface and comprising:
      a plurality of semiconductor Hall devices provided under the sensor surface, the Hall devices being arranged in X rows and Y columns, X and Y being integers greater than or equal to one, the Hall devices having surfaces; and
      second molecular receptors immobilized on the Hall devices having surfaces;
   a selection means for selecting individual ones of the Hall devices and for extracting outputs of the selected Hall devices; and
   a signal processing means for;
      comparing only the extracted outputs to determine which of the selected Hall devices have magnetic molecules bound to the second molecular receptors thereof and which of the selected Hall devices do not have magnetic molecules bound to the second molecular receptors thereof; and
      analyzing the compared extracted outputs to determine the amount of measurement objects in the material.

2. The biosensor according to claim 1, wherein the surface of the magnetic sensor includes a reference region to which the magnetic molecules are incapable of binding, and the signal processing means conducts a comparison using an intensity of a magnetic field of the reference region as a reference.

3. The biosensor according to claim 2, wherein a surface treatment is performed on the reference region such that molecular receptors are incapable of binding thereto.

4. The biosensor according to any one of claims 1 to 3, wherein the magnetic sensor, the selection means, and a signal amplifier circuit that amplifies an output signal of a selected one of the plurality of semiconductor Hall devices are formed on one chip.

5. The biosensor according to claim 1, wherein a size of each detection space in which detection of a magnetic field by a corresponding one of the plurality of semiconductor Hall devices is possible is equal to a size of approximately one molecule of the magnetic molecules for binding.

6. The biosensor according to claim 1, wherein, in the magnetic sensor, the plurality of semiconductor Hall devices are arranged at intervals such that adjacent ones of the plurality of semiconductor Hall devices detect mutually different ones of the magnetic molecules.

7. The biosensor according to claim 6, wherein the adjacent ones of the plurality of semiconductor Hall devices are arranged at an interval that is equal to or greater than a size of the magnetic molecules.

8. The biosensor according to claim 1, wherein the surface of the magnetic sensor is subjected to a surface treatment for selectively immobilizing the second molecular receptors in selected regions on the surface of the sensor.

9. The biosensor according to claim 8, further comprising recesses of a size corresponding to a size of the magnetic molecules provided on the surface of the magnetic sensor, and the second molecular receptors that bind to the magnetic molecules are provided only in the recesses.

10. The biosensor according to claim 8 or 9, wherein a thin gold film is formed in regions on the surface of the magnetic sensor, and selected ones of the second molecular receptors having an end modified by a thiol group, the selected ones of the second molecular receptors being immobilized.

11. The biosensor according to claim 1, wherein the biosensor further comprises a magnetic field generation means arranged in a position facing the surface of the magnetic sensor, the magnetic field generation means generating an applied magnetic field, which is applied to the surface of the magnetic sensor.

12. The biosensor according to claim 11, wherein the magnetic field generation means further comprises a means for intermittently generating the applied magnetic field.

13. The biosensor according to claim 11 or 12, wherein the magnetic field generation means further comprises a detector circuit for generating a magnetic field at a constant frequency, and extracting a frequency component corresponding to one of a plurality of magnetic fields, said one of the plurality of magnetic fields being associated with an output signal of the detector circuit.

14. The biosensor according to claim 1, wherein the biosensor further comprises a magnetic field generation means arranged on a backside of the magnetic sensor, the magnetic field generation means generating an applied magnetic field that is applied to the surface of the magnetic sensor.

15. The biosensor according to claim 14, wherein the magnetic field generation means further comprises a means for intermittently generating the applied magnetic field.

16. The biosensor according to claim 14 or 15, wherein the biosensor further comprises a detector circuit, which, when the magnetic field generation means generates the applied magnetic field at a constant frequency, and the detector circuit extracts a frequency component corresponding to the applied magnetic field from an output signal of the detector element.

17. The biosensor according to claim 1, wherein the surface of the magnetic sensor faces a direction in which gravitational force acts.

18. The biosensor according to claim 1, wherein each of the plurality of semiconductor Hall devices has a pair of current terminals, a gate electrode controlling current flowing between the current terminals, and a pair of output terminals arranged such that current flows substantially perpendicular to current flowing between the pair of current terminals.

19. The biosensor according to any one of claims 1 to 3, wherein each of the plurality of semiconductor Hall devices has a pair of current terminals, a gate electrode for controlling current flowing between the current terminals, and a pair of output terminals arranged such that current flows substantially perpendicular to current flowing between the current terminals, and wherein the gate electrode is connected to a gate electrode wire that is common to first selected ones of the plurality of semiconductor Hall devices arranged in a column, the pair of current terminals are connected to a pair of current terminal wires that are common to second selected ones of the plurality of semiconductor Hall devices arranged in a row, the pair of output terminals are connected to a pair of output terminal wires that are common to the second selected ones of the plurality of semiconductor Hall devices, and the selection means extracts an output signal of corresponding to any one of the plurality of semiconductor Hall devices by selecting the gate electrode wire, the pair of current terminal wires, and the pair of output terminal wires.

\* \* \* \* \*